United States Patent
Clemons et al.

(10) Patent No.: US 9,541,558 B2
(45) Date of Patent: Jan. 10, 2017

(54) CYSTEINE HYDRAZIDE NICOTINAMIDE FOR GLYCOMICS AND GLYCOPROTEOMICS USES

(71) Applicant: California Institute of Technology, Pasadena, CA (US)

(72) Inventors: William M. Clemons, Pasadena, CA (US); Kyoung-Soon Jang, Pasadena, CA (US); Roger Nani, Pasadena, CA (US); Sergiy Levin, North Wales, PA (US); Sarah Reisman, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 340 days.

(21) Appl. No.: 14/017,744

(22) Filed: Sep. 4, 2013

(65) Prior Publication Data
US 2014/0072981 A1 Mar. 13, 2014

Related U.S. Application Data

(60) Provisional application No. 61/697,096, filed on Sep. 5, 2012, provisional application No. 61/712,703, filed on Oct. 11, 2012.

(51) Int. Cl.
*G01N 33/68* (2006.01)

(52) U.S. Cl.
CPC ...... *G01N 33/6848* (2013.01); *G01N 33/6842* (2013.01); *Y10T 436/143333* (2015.01)

(58) Field of Classification Search
CPC ........... G01N 33/6848; G01N 33/6842; Y10T 436/143333
See application file for complete search history.

(56) References Cited

PUBLICATIONS

Miura et al. BlotGlycoABCTM, an integrated glycoblotting technique for rapid and large scale clinical glycomics. Mol. Cell Proteomics. 2008, vol. 7, pp. 370-377.*

Jang, Kyoung-Soon, et al. "A Cationic Cysteine-Hydrazide as an Enrichment Tool for the Mass Spectrometric Characterization of Bacterial Free Oligosaccharides," Anal Bioanal Chem., 407(20): 6181-6190 (Aug. 2015).

Kyoung-Soon Jang, et al., "A Versatile Enrichment Tool for Bacterial Glycomics and Glycoproteomics: a cationic cysteine hydrazide-functionalized resin"; Poster Presentation, Presented May 24, 2012, American Society of Mass Spectrometry Conference; Vancouver, BC, Canada.

* cited by examiner

*Primary Examiner* — Shafiqul Haq
(74) *Attorney, Agent, or Firm* — Foley Hoag LLP; David P. Halstead

(57) ABSTRACT

A cysteine hydrazide nicotinamide (Cyhn) reagent designed for the enrichment of bacterial glycoproteins is provided. Methods for purification of free oligosaccharides and their analysis are also provided.

3 Claims, 37 Drawing Sheets

CYSTEINE HYDRAZIDE NICOTINAMIDE FOR GLYCOMICS AND GLYCOPROTEOMICS USES

CROSS-REFERENCE TO RELATED APPLICATIONS

The present application claims the benefit of U.S. Provisional Application No. 61/697,096 filed on Sep. 5, 2012 and U.S. Provisional Application No. 61/712,703 filed on Oct. 11, 2012, each of which is incorporated herein by reference in its entirety.

STATEMENT REGARDING FEDERALLY SPONSORED RESEARCH OR DEVELOPMENT

This invention was supported in part by the United States Government under National Science Foundation Career grant 1057143 and National Institutes of Health Pioneer Award 5DP1GM105385. The Government may have certain rights in this invention.

BACKGROUND OF THE INVENTION

The identification of an organism's total glycosylated protein pool, the glycoproteome, requires selectively and efficiently isolating glycoproteins from biological samples. Various enrichment techniques, such as lectin affinity chromatograpy (Madera et al., (2008) *J Sep Sci* 31, 2722-2732; Mechref et al., (2008) *Methods Mol Biol* 424, 373-396), metabolic tagging/click chemistry (Dube et al., (2003) *Curr Opin Chem Biol* 7, 616-625; Laughlin et al. (2006) *Methods Enzymol* 415, 230-250), and periodate oxidation/hydrazide chemistry (Zhang et al., (2003) *Nat Biotechnol* 21, 660-666), have been established for studies in eukaryotes. Among these, chemical coupling by hydrazide chemistry is the most generally applicable. Originally introduced by Zhang and colleagues (Zhang et al., 2003) *Nat Biotechnol* 21, 660-666), periodate oxidizes the cis-diol of glycans to aldehydes which can then be coupled to a hydrazide resin to form a stable hydrazone bond. The captured glycoprotein can then be analyzed by mass spectrometry. The limitation of this method is the requirement of an enzyme to release enriched protein from functionalized resins. Peptide:N-glycosidase F (PNGase F) has been commonly used for this; however, it cannot cleave the equivalent bonds in most bacterial glycoproteins.

In Campylobacterales and related ε-proteobacteria with N-linked glycosylation (NLG) pathways, free oligosaccharides (fOS) are released into the periplasmic space from lipid-linked precursors by the bacterial oligosaccharyltransferase (PglB). This central role makes the PglB protein a hallmark of the likely existence of NLG in an organism and, based on this, genome analysis identified PglB orthologs in numerous bacteria (Nothaft et al. (2010) Microbiology 8:765-778). These include a number of additional bacterial families including some non-ε-proteobacteria. While the presence of PglB is a useful marker, empirical evidence is required to prove NLG exists in a given organism. In certain bacteria, such evidence remains difficult to obtain and full oligosaccharide remains to be determined Free oligosaccharides (fOS) were exploited to demonstrate diverse glycostructures across a variety of *Campylobacter* and related species (Nothaft et al. (2012) Mol. Cell. Proteomics 11:1203-1219). In the periplasmic space of *C. jejuni*, free heptasaccharide, structurally identical to that found as an N-linked glycan counterpart, is found that is presumed to be the result of an additional hydrolase activity of PglB (Nothaft et al. (2009) Proc. Natl. Acad. Sci. USA 106:15019-150240). Given these observations, one would hypothesize that identification of fOS from the periplasmic extracts of more distant bacteria would allow prediction of the N-linked glycan structure and provide strong evidence for the broad existence of bacterial NLG systems. This is limited by the need for selective enrichment of fOS from periplasmic extracts and then subsequent structural characterization.

Therefore, there remains a need to identify oligosaccharides from more organisms and in a robust and facile way, using enrichment techniques that do not require the use of a PNGase F.

SUMMARY OF THE INVENTION

In lieu of a functional enzyme, we have developed new chemical probes to take advantage of the hydrazide chemistry. Our probes have been designed to possess thiol and cationic moieties in addition to the hydrazide group (FIG. 1). The thiol group is used for conjugation to a thiol-activated solid support, which can be released under reducing conditions after glycoprotein capture. The addition of the positive charge provides an improved ionization signal during MS analysis.

The enrichment technique of the invention enables efficient identification of bacterial free glycans and glycoproteins as well as eukaryotic glycoproteins. The cationic hydrazide functionalized resins was able to selectively capture bacterial glycoproteins and free oligosaccharides in periplasmic fractions of *C. jejuni* as well as glycoproteins from human cancer cells, followed by mass spectrometric analysis. This method provides simple and sensitive ways necessary for comprehensive glycomic and glycoproteomic studies.

Using this enrichment technique followed by MS/MS analysis, we successfully isolated and identified periplasmic fOS from *Campylobacter* and *Desulfovibrio* species. This utilizes a hydrazide-functionalized resin that also contains a methylated nicotinamide structure, providing a fixed cationic charged probe producing predominantly singly charged ions during MS analysis. The complementary CID, IRMPD and EID techniques allowed us to interpret unknown bacterial fOS structures.

In one aspect, the invention provides a compound of Formula (I):

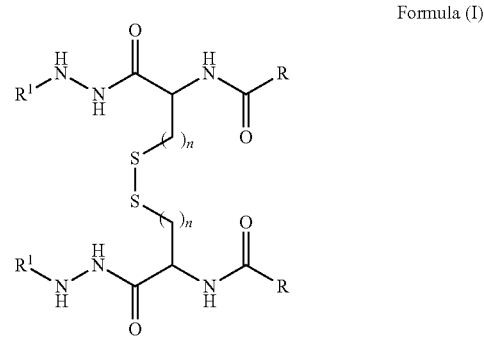

Formula (I)

or a salt thereof, wherein:
n is an integer from 1-10;
R is a nitrogen-containing ring capable of forming a salt; and
$R^1$ is H or saccharide.

In another aspect, the invention provides a compound of Formula (II):

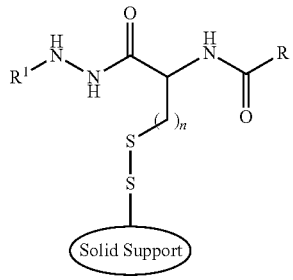

Formula (II)

or a salt thereof, wherein:
n is an integer from 1-10;
R is a nitrogen-containing ring capable of forming a salt; and
R¹ is H or saccharide.

In another aspect, the invention provides a compound of Formula (III):

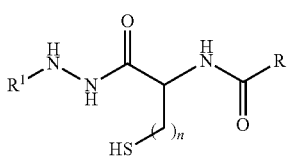

Formula (III)

or a salt thereof, wherein:
n is an integer from 1-10;
R is a nitrogen-containing ring capable of forming a salt; and
R¹ is H or saccharide.

In certain embodiments of the above formulae, if R is a six-membered heteroaryl ring, it is not a 3-pyridyl ring and/or the number of nitrogen atoms present in the ring is at least 2.

In certain preferred embodiments, R is 3-pyridyl.

In certain preferred embodiments, n=1.

In one aspect, the invention provides a method for preparing a compound of Formula (I):

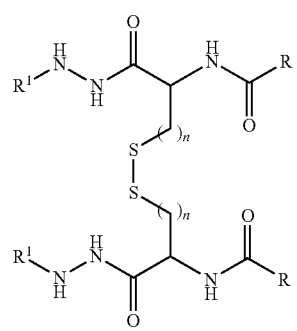

Formula (I)

or a salt thereof, wherein:
n is an integer from 1-10;
R is a nitrogen-containing ring capable of forming a salt; and
R¹ is H;
wherein the method comprises dimerizing a compound of Formula (IV) in the presence of an oxidizing agent

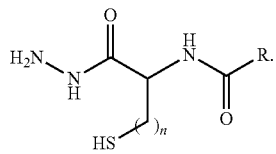

Formula (IV)

In one aspect, the invention provides a method for preparing a compound of Formula (II):

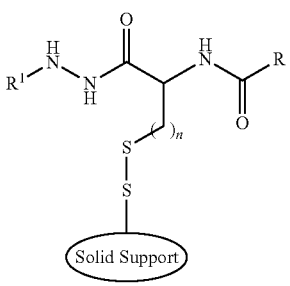

Formula (II)

or a salt thereof, wherein:
n is an integer from 1-10;
R is a nitrogen-containing ring capable of forming a salt; and
R¹ is saccharide;
wherein the method comprises reacting a compound of Formula (V) with a saccharide under reductive amination conditions

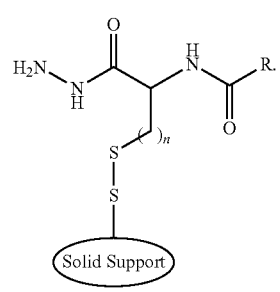

Formula (V)

In one aspect, the method comprises reacting in the presence of a base a compound of Formula (IV) with a thiol-activated solid support to provide a compound of Formula (V) (both as defined above).

In one aspect, the invention provides a method for preparing a compound of Formula (IV), comprising reacting a compound of Formula (VI) with hydrazine

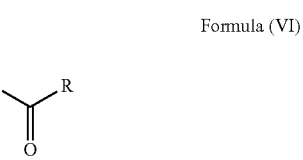

Formula (VI)

to provide a compound of Formula (IV).

In certain embodiments of the above methods, if R is a six-membered heteroaryl ring, it is not a 3-pyridyl and/or the number of nitrogen atoms present in the ring is at least 2.

In certain certain preferred embodiments of the above methods, R is 3-pyridyl.

In certain certain preferred embodiments of the above methods, n=1.

In one aspect, the invention provides a method for separating one or more oligosaccharides or glycoproteins from a solution, comprising reacting a compound of Formula (II)

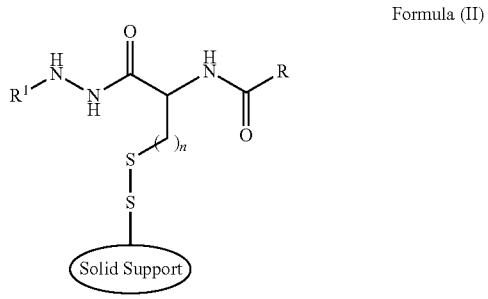

Formula (II)

or a salt thereof, wherein:
n is an integer from 1-10;
R is a nitrogen-containing ring capable of forming a salt; and
$R^1$ is H;
with a solution comprising one or more oligosaccharides or glycoproteins (e.g., under reductive alkylation conditions) to provide a compound of Formula (II) wherein $R^1$ is saccharide.

In certain preferred embodiments, the method comprises reacting a compound of Formula (II) wherein $R^1$ is saccharide with an alkylating agent, such as a methylating agent or methylation reagent, such as methyl iodide.

In one aspect, the invention provides a method for analyzing a saccharide comprising subjecting a compound of Formula (III) to mass spectrometry

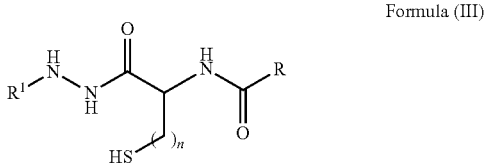

Formula (III)

or a salt thereof, wherein:
n is an integer from 1-10;
R is a nitrogen-containing ring capable of forming a salt; and
$R^1$ is saccharide.

In certain embodiments, the saccharide is an oligosaccharide.

In certain embodiments, the method comprises preparing a compound of Formula II wherein $R^1$ is an oligosaccharide from a compound of Formula II wherein $R^1$ is H, e.g., as described above, e.g., by reacting the compound of Formula II wherein $R^1$ is a saccharide with a saccharide under reductive conditions. In certain embodiments, further the method comprises releasing a compound of Formula III from the solid support under reductive conditions (e.g., using DTT). In certain such embodiments, the method further comprises reacting the compound (e.g., the compound of Formula II wherein $R^1$ is a saccharide or the compound of Formula III) with a methylating agent as described above.

In certain embodiments, the method comprises using complementary tandem mass spectrometry analyses.

In certain embodiments, the method comprises using MS/MS mass spectrometry analyses.

In certain embodiments, the method comprises using infrared multiphoton dissociation (IRMPD).

In certain embodiments, the method comprises using electron induced dissociation (EID).

In certain embodiments, the method comprises using MS/MS mass spectrometry, IRMPD and EID in combination.

DETAILED DESCRIPTION OF THE INVENTION

Figure 1A:
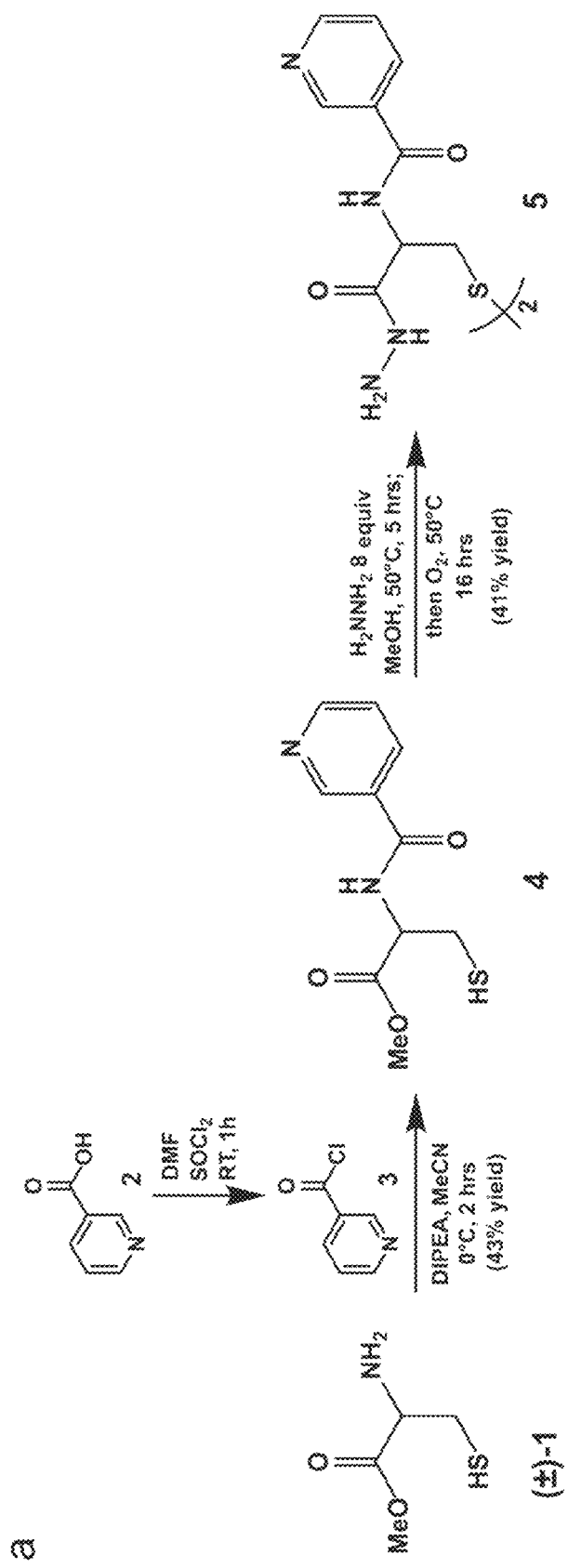
FIG. 1A shows the synthetic route to prepare cationic hydrazide-functionalized resin via cysteine hydrazide nicotinamide.

The methods depicted herein are suitable for sequencing saccharides, such as starches, arabinoxylans, and pectins. In some embodiments, the saccharide can be an oligosaccharide, such as fructo-oligosacharides, galacto-oligosaccharides, and mannan oligosaccharides. Generally speaking, any saccharide or oligosaccharide capable of undergoing a reductive amination reaction can be sequenced using the compositions and methods disclosed herein.

I. DEFINITIONS

The terms "halogen", "halide" and "halo", as used herein, mean halogen and include fluoro, chloro, bromo and iodo.

The terms "hydroxyl" or "hydroxy" refer to the group —OH.

The term "alkyl" refers to the radical of saturated aliphatic groups, including straight-chain alkyl groups, and branched-chain alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. In certain embodiments, alkyl groups are lower alkyl groups, e.g., methyl, ethyl, n-propyl, i-propyl, n-butyl and n-pentyl.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. In certain embodiments, a straight chain or branched chain alkyl has 30 or fewer carbon atoms in its backbone (e.g., $C_1$-$C_{30}$ for straight chains, $C_3$-$C_{30}$ for branched chains). In preferred embodiments, the chain has ten or fewer carbon ($C_1$-$C_{10}$) atoms in its backbone. In other embodiments, the chain has six or fewer carbon ($C_1$-$C_6$) atoms in its backbone.

Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aryl or heteroaryl moiety.

The terms "amine" and "amino" are art-recognized and refer to both unsubstituted and substituted amines and salts thereof, e.g., a moiety that can be represented by

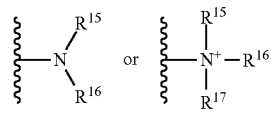

wherein $R^{15}$, $R^{16}$, and $R^{17}$ each independently represent a hydrogen or a hydrocarbyl group, or $R^{15}$ and $R^{16}$ taken together with the N atom to which they are attached complete a heterocycle having from 4 to 8 atoms in the ring structure.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. "Nitrogen-containing heteroaryl" refers to heteroaryl wherein any heteroatoms are N. The term "heteroarylene" refers to a divalent heteroaryl.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. Heterocyclyl groups include, for example, piperidine, piperazine, pyrrolidine, morpholine, lactones, lactams, and the like.

The term "methylating agent" or "methylation reagent" refers to a reagent capable of reacting with a nucleophilic functional group, such as a basic nitrogen atom, to add a methyl group to the functional group. Examples of methylating agents are iodomethane (methyl iodide), bromomethane, chloromethane, dimethyl sulfate, methyl toluenesulfonate, methyl trifluoromethanesulfonate (methyl triflate), dimethylcarbonate, methyl fluorosulfonate (magic methyl). In certain embodiments, the reagent may add an isotopically labeled methyl group, e.g., having a $^{13}$C or $^{14}$C carbon atom and/or one or more deuterium or tritium atoms (i.e., at an abundance at least 10 times the natural abundance of the heavy isotope, preferably at an abundance of at least 90%, at least 95%, or at least 98% of the atoms in the reactive methyl group(s) of the methylating agent).

The term "counterion" refers to the ion that accompanies an ionic species to maintain charge neutrality. Examples of negatively charged counterions are $Cl^-$, $Br^-$, $I^-$, $F^-$, $BF_4^-$. Examples of positively charged counterions are $H^+$, $Li^+$, $Na^+$, $Mg^{2+}$, $Ca^{2+}$.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. Examples of straight chain or branched chain lower alkyl include methyl, ethyl, isopropyl, propyl, butyl, tertiary-butyl, and the like.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety.

The term "solid support" denotes any particle, bead, resin, or surface bearing functional groups capable of reacting with solution-phase molecules and such solid supports that have been reacted with such solution-phase molecules. Examples of solid supports are inorganic supports and organic supports, such as silica gel, glass (e.g., controlled-pore glass), polyethylene glycol/dimethylacrylamide copolymer (PEGA), crosslinked polystyrene resins, TentaGel™, Argo-Gel™, cellulose, Wang resin, and Rink amide resin.

Unless specifically stated as "unsubstituted," references to chemical moieties herein are understood to include substituted variants. For example, reference to an "alkyl" group or moiety implicitly includes both substituted and unsubstituted variants.

At various places in the present specification substituents of compounds of the invention are disclosed in groups or in ranges. It is specifically intended that the invention include each and every individual subcombination of the members of such groups and ranges. For example, the term "$C_1$-$C_6$ alkyl" is specifically intended to individually disclose methyl, ethyl, propyl, isopropyl, n-butyl, sec-butyl, isobutyl, etc.

For a number qualified by the term "about", a variance of 2%, 5%, 10% or even 20% is within the ambit of the qualified number.

II. SYNTHETIC PREPARATION

The compounds disclosed herein can be prepared in a variety of ways known to one skilled in the art of organic synthesis, and in analogy with the exemplary compounds whose synthesis is described herein. The starting materials used in preparing these compounds may be commercially available or prepared by known methods. Preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis*, 44th. Ed., Wiley & Sons, 2006, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

A probe can be attached to the solid support by means of a functional unit. Functional units (linkers) are known in the art as chemical moieties comprising a covalent bond or a chain/ring of atoms that covalently attach a solid support to a chemical structure (e.g., the probe). Examples of functional units are succinyl, carbonate, carbamate, disulphide (e.g., thiol-activated), amino group, benzhydrylamine (BHA), trityl.

Reductive amination is well known in the art and comprises reacting a carbonyl group such as a ketone or aldehyde, with an amine to form an imine or iminium intermediate that is reduced by a reducing agent, such as $LiAlH_4$, $NaBH_4$, $NaCNBH_3$, $NaBH(OAc)_3$, DIBAL-H or Lindlar catalyst, to the corresponding amine Many suitable conditions, compatible with a variety of solvents and functional groups, are available and any suitable conditions can be employed in the methods discussed herein.

Oxidizing agents, reagents capable of accepting electrons from other molecules or atoms, are well known in the art and. Examples of oxidizing agents are oxygen ($O_2$), hydrogen peroxide, potassium permanganate, hypochlorite salts, elemental halogens (such as iodine), salts of oxidized metals (such as salts of Fe(III) or Cu(II)), osmium tetroxide and sulfuric acid.

Disulfide cleavage agents are well known in the art and capable of cleaving disulfide bonds to release a thiol. Examples of disulfide cleavage agents are dithiothreitol (DTT or Cleland's reagent), 2-mercaptoethanol, dithiobutylamine, and $NaBH_4$.

Compounds of Formula (V) may be prepared by reacting a compound of Formula (IV) with a thiol-activated solid support in the presence of a base. This chemical reaction comprises attack of thiolate group ($RS^-$) onto a sulfur atom of the support-bound disulfide bond, thereby forming a new disulfide bond. This reaction is also known as thiol-disulfide exchange.

The compounds of Formula (III) can be submitted for MS analysis as neutral compounds or alkylated compounds (salts). The nitrogen-containing ring in the compounds of Formula (III) is capable of forming a salt (such as by undergoing alkylation, e.g., methylation), thereby carrying a positive charge. The positive charge improves the ionization signal during MS analysis compared to that of the neutral compounds, thereby facilitating MS analysis.

III. EXPERIMENTAL

The invention will be more readily understood by reference to the following examples which are included merely for purposes of illustration of certain aspects and embodiments of the present invention, and are not intended to limit the invention.

Preparation of Cationic Cysteine Hydrazide Derivative and Functionalized Resins.

To synthesize cysteine hydrazide nicotinamide (Cyhn) 6, a straightforward two-step sequence was introduced (FIG. 1a). Racemic cysteine methyl ester (1) was coupled with the acid chloride of nicotinic acid, affording cysteine methyl ester nicotinamide (4). Unreacted cysteine methyl ester was removed using solution-phase extraction, and the major impurity of the reaction (acylation of the thiol group of the product) was separated by silica column chromatography. Reaction of the cysteine methyl ester nicotinamide with excess hydrazine hydrate in methanol resulted in the Cyhn compound (6). The reaction was monitored by LC/MS, and upon complete consumption of the starting material the solution was sparged with oxygen gas to effect dimerization of the Cyhn monomer. Precipitation of Cyhn dimer resulted during this process, and after concentration and trituration with methanol the Cyhn dimer (5) was obtained in >95% purity. The identity of the intermediates and final product was confirmed by $^1H$ and $^{13}C$ NMR, IR, and HRMS (FIG. 6-11).

Figure 1B:
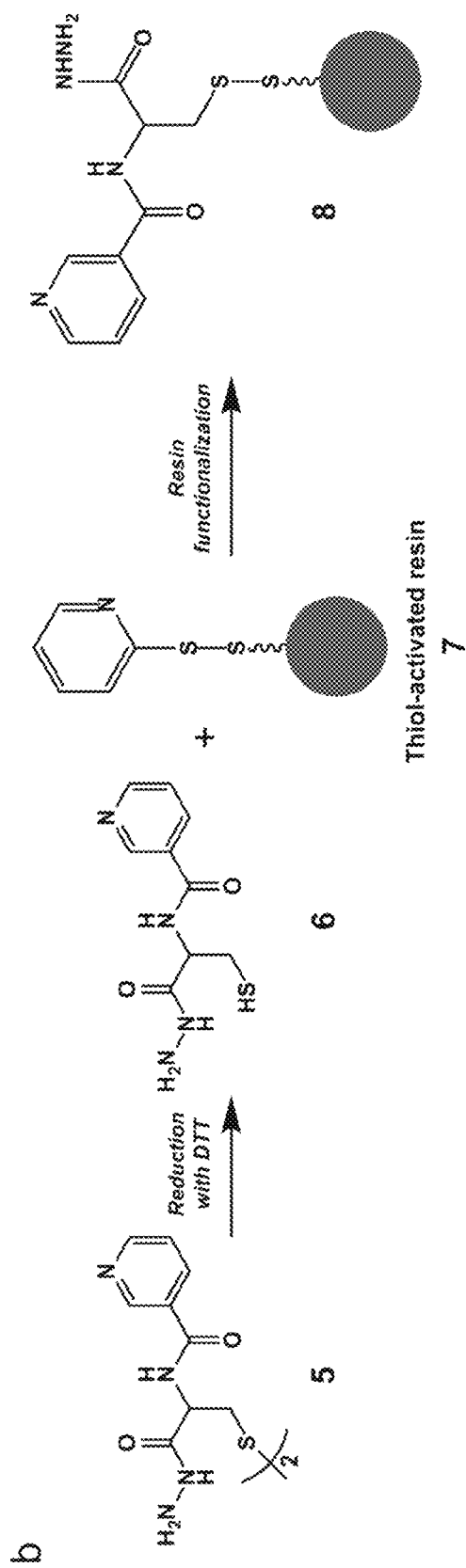
FIG. 1B shows the synthetic route to prepare cationic hydrazide-functionalized resin via conjugation to thiol-activated resins.

In the course of our studies we observed that ester 4 is stable as the free thiol; the Cyhn monomer 6, however, was very susceptible to oxidation to the disulfide. This feature of hydrazide 6 greatly hampered the attempted isolation and purification of this compound. Alternatively, the Cyhn dimer (5) existed as a stable solid that could be reliably produced in high purity. The stability and ease of purification of the Cyhn dimer was exploited to obtain gram quantities of a Cyhn monomer precursor. Prior to the conjugation, the disulfide moiety of the Cyhn-dimer was reduced with dithiothreitol (DTT) and the liberated monomer was used in situ for conjugation to the activated thiol resins (FIG. 1b). The pyridyl group serves as a handle for forming a cationic species, facilitating mass spec analysis of various conjugated species. The Cyhn compound was conjugated onto commercially available thiol-activated solid supports such as thiopropyl Sepharose™ 6B resins or BcMag™ thiol-activated magnetic beads, resulting in the Cyhn-6B or Cyhn-BcMag resins, respectively. The prepared Cyhn resins were employed to selectively conjugate free oligosaccharides as well as oxidized glycoproteins from mixtures as demonstrated in FIG. 2.

Identification of Bacterial Periplasmic Free Oligosaccharide (fOS) of *C. jejuni*

Periplasmic samples were fractionated from osmotically shocked *C. jejuni* NCTC11168. Initially, fOS were enriched using a standard method (Liu et al., (2006) Analytical Chemistry 78:6081-6087) involving binding to a solid-phase Carbograph™ extraction cartridge followed by elution. This eluate was used in a MALDI-TOF MS analysis resulting in peak that corresponded to the expected heptasaccharide (FIG. 13B); however, the noise associated with this purification included a number of additional significant peaks. Recently, an enrichment strategy was developed using cysteine hydrazide nicotinamide (Cyhn)-functionalized resins that allows for selective purification of oligosaccharides with free reducing ends (K. S. Jang et al., submitted for publication). The fOS from the enriched fraction were covalently bound to the resin through the hydrazide moiety generating fOS-Cyhn conjugate that were released under reducing conditions (see FIG. 2a). This sample was analyzed by MALDI-TOF and the resulting spectrum contained the observed mass-to-charge (m/z) value at 1660.4 from the periplasmic sample of C. jejuni agreed well with the predicted mass of the heptasaccharide-Cyhn conjugate (FIG. 13C). The mass difference of 214 Da represents the fOS$_{Cj}$ covalently conjugated via hydrazone formation to a methylated Cyhn moiety. This significantly improved the signal-to-noise in the MS analysis and confirmed the expected fOS$_{Cj}$ from this strain including the presence of a reducing end sugar.

Structural information for the enriched fOS$_{Cj}$-Cyhn was obtained from MS/MS analysis using collision induced dissociation (CID). For this, fragment ions of the abundant precursor ion at m/z 1660.60 were identified by tandem mass spectrometry (FIG. 13D). As expected (25, 26), CID spectra resulted predominantly in glycosidic bond cleavages revealing the monosaccharide composition of the fOS$_{Cj}$, which comprises the branched heptasaccharide (GalNAc-GalNAc-[Glc]-GalNAc-GalNAc-GalNAc-diNAcBac) as previously seen (Linton et al. (2005) Mol. Microbiol. 55:1695-1703; Wacker et al. (2002) Science 298:1790-1793), where diNAcBac (2,4-diacetamido-2,4,6-trideoxyglucose) is a diacetylated bacillosamine. These results demonstrate the robustness of the Cyhn conjugation as a tool for enriching free oligosaccharides.

Figure 13A:
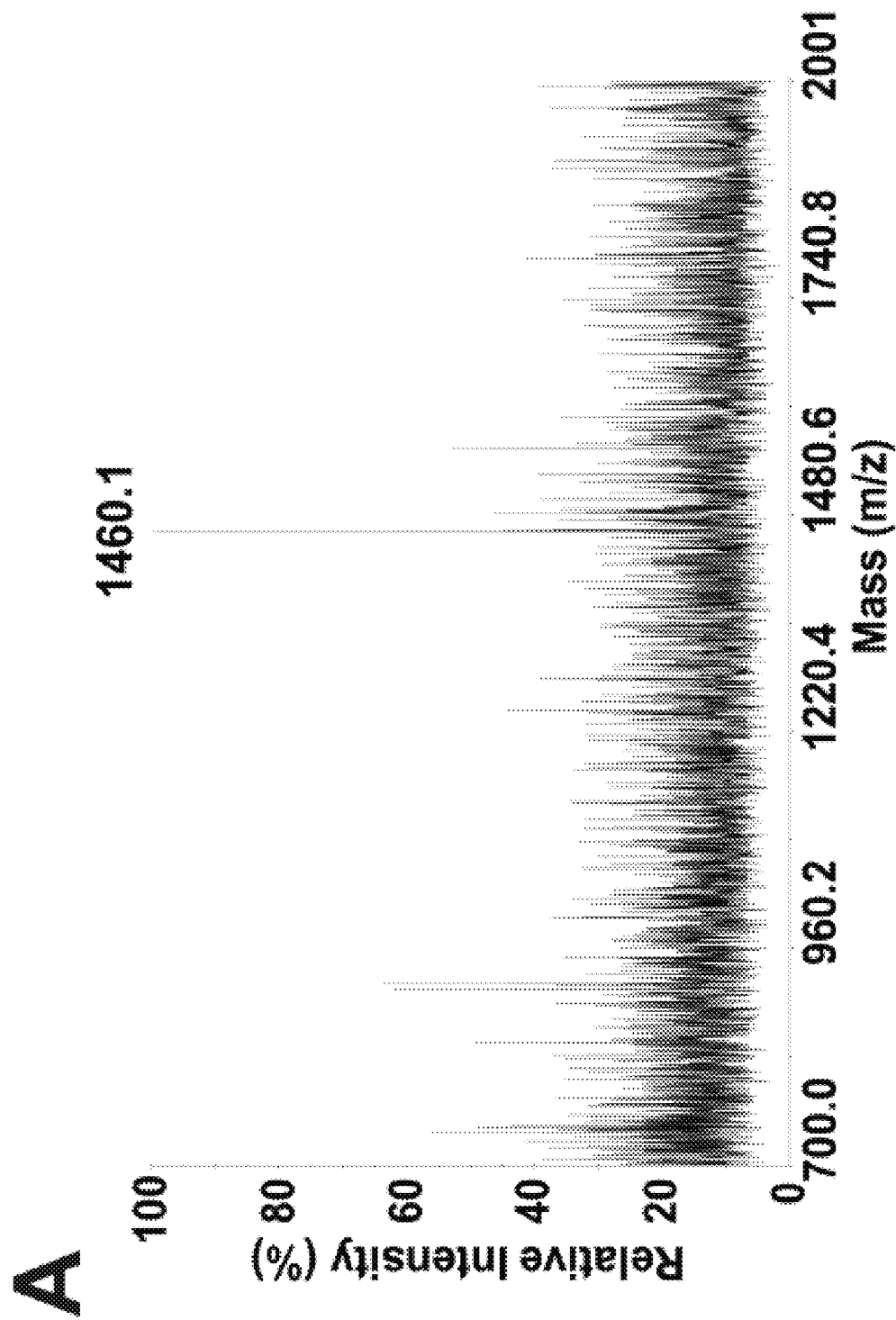
FIG. 13A shows the MALDI-TOF MS spectrum of enriched fOS$_{Cc}$. The enrichment was performed with periplasmic extracts from *C. concisus* by solid-phase extraction.
Figure 13B:
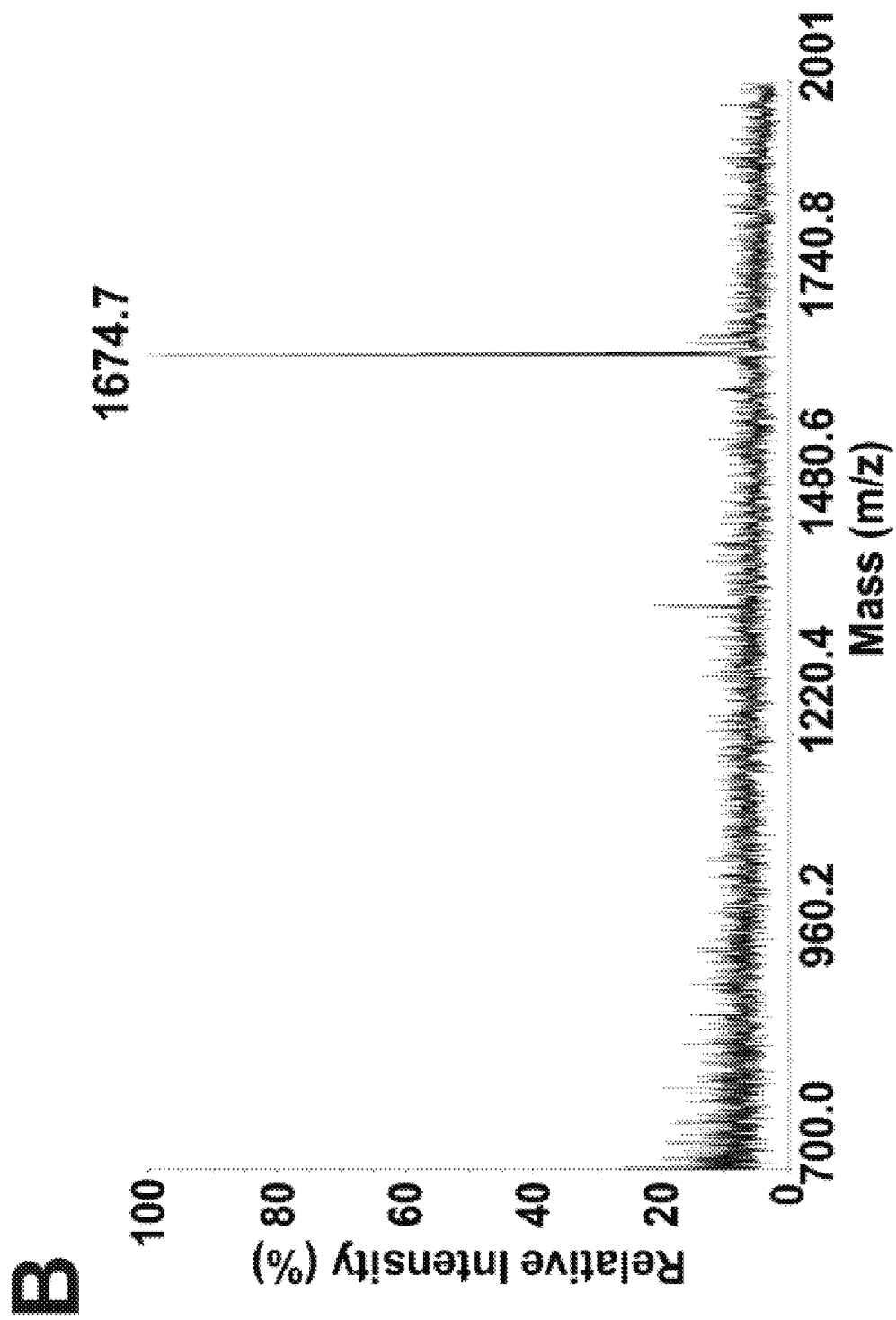
FIG. 13B shows the MALDI-TOF MS spectrum of enriched fOS$_{Cc}$. The enrichment was performed with periplasmic extracts from *C. concisus* by the hydrazide-functionalized resins.
Figure 13C:
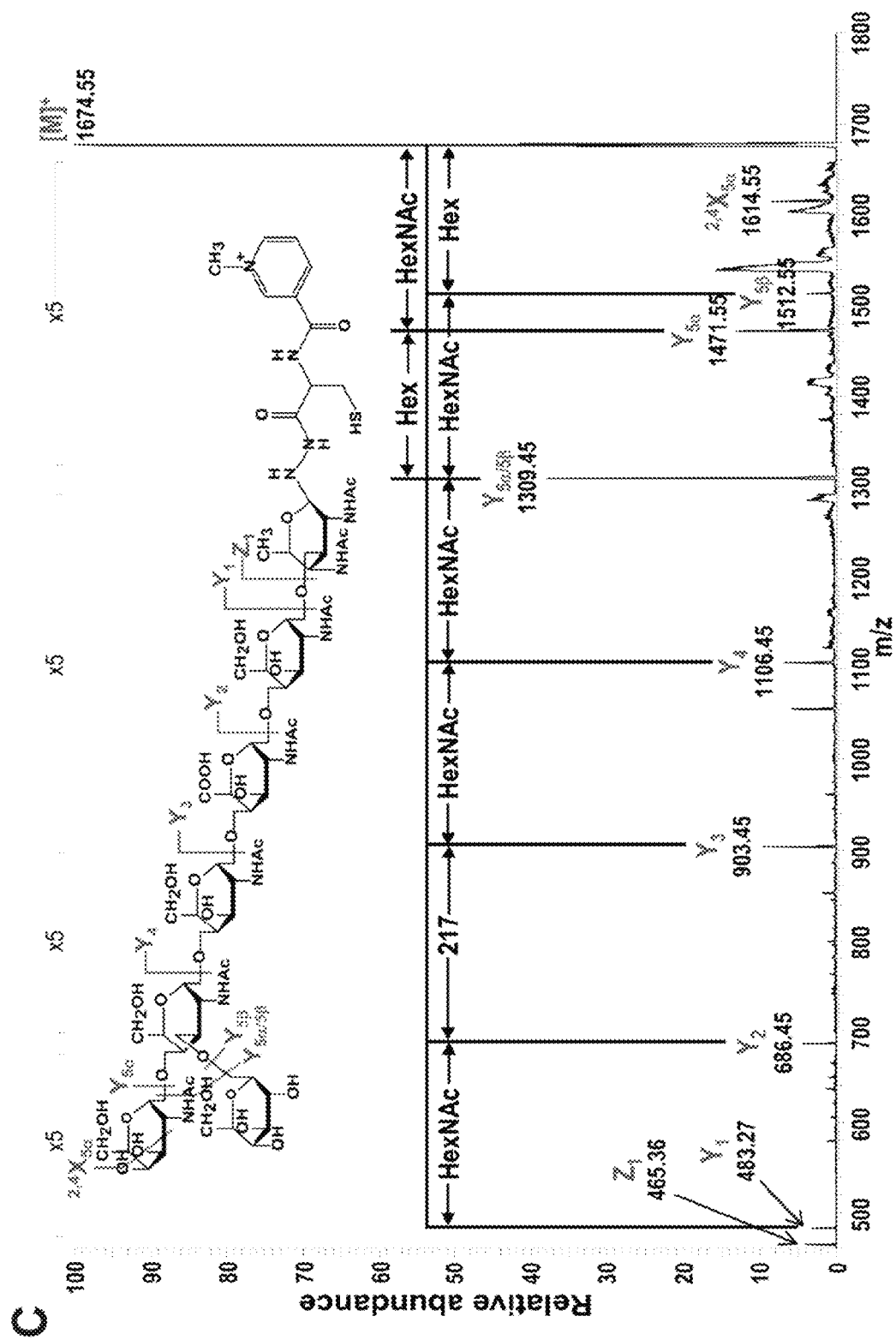
FIG. 13C shows the CID MS/MS spectrum of the fOS$_{Cc}$ from *C. concisus* (CID 30-ms irradiation with 15% collision energy).
Figure 13D:
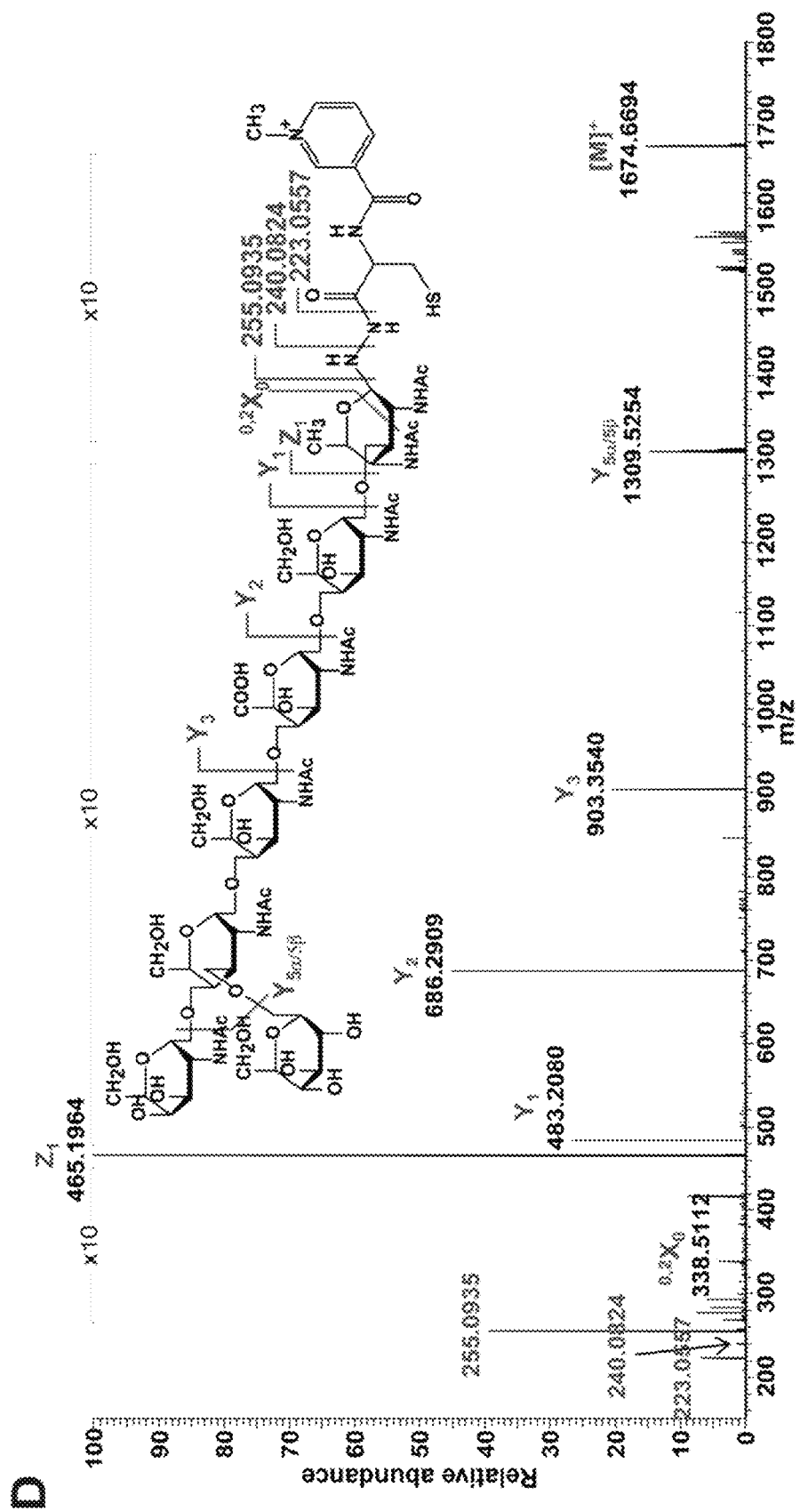
FIG. 13D shows the IRMPD MS/MS spectrum of the fOS$_{Cc}$ from *C. concisus* (IRMPD 50-ms with 10-W laser power).
Figure 13E:
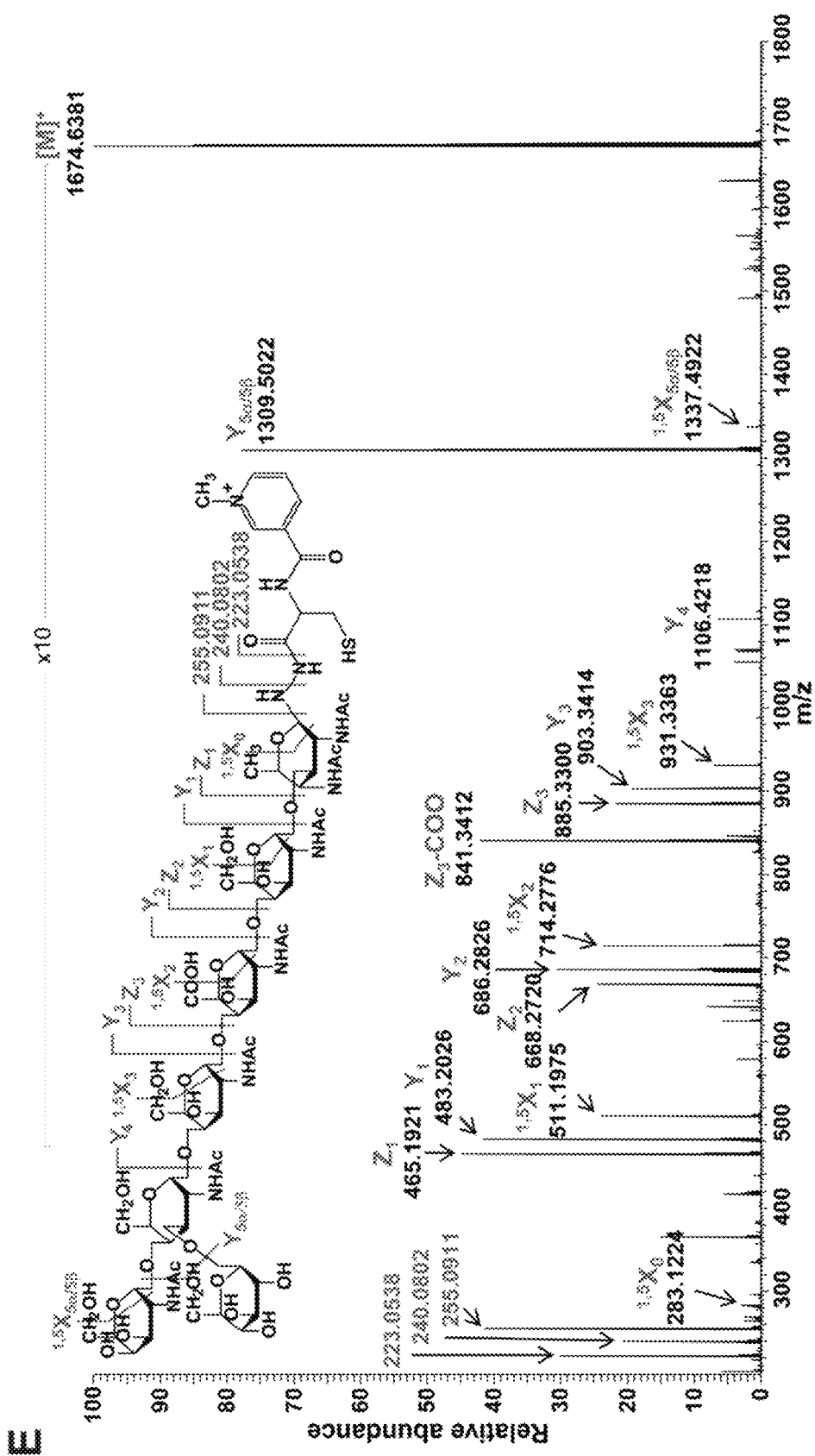
FIG. 13E shows the EID MS/MS spectrum of the fOS$_{Cc}$ from *C. concisus* (EID 30-ms with a voltage of −20 V).

Structural Characterization of fOS of C. concisus by Complementary MS/MS Analyses To resolve the different reported fOS from C. concisus, a solid phase extracted periplasmic fOS$_{Cc}$ from C. concisus RM5485 was identified by MS at m/z 1460.1 (FIG. 13A). Using the Cyhn conjugation, we could further enrich this fraction resulting in a peak at m/z 1674.7 consistent with a heptasaccharide conjugated to a Cyhn moiety (FIG. 13B). To obtain further structural information, this abundant precursor ion was subjected to CID MS/MS analysis that generated predominantly free oligosaccharides consistent with a branched heptasaccharide (i.e. HexNAc-(Hex)-HexNAc-HexNAc-217-HexNAc-228) (FIG. 13C). The mass of 228 was consistent with diNAcBac that had previously been identified for C. jejuni and, based on the operon structure, is expected for C. concisus. The MS/MS analysis using different fragmentation techniques such as infrared multiphoton dissociation (IRMPD) (Little et al., (1994) Anal. Chem. 66:2809-2815; Woodin et al., (1978), J. Am. Chem. Soc. 100:3248-3250) and electron induced dissociation (EID) (Budnik et al. (2003) Anal. Chem. 75:5994-6001; Wolff et al (2008) J. Am. Soc. Mass. Spectrom. 19:1449-1458; Kalli et al., (2011) J. Am. Soc. Mass Spectrom. 22:2209-2221; Gord et al., (1993) J. Am. Soc. Mass. Spectrom. 4:145-151) along with CID were complementarily used for the structural elucidation of fOS$_{Cc}$. Particularly, IRMPD and EID MS/MS analysis identified the existence of the enrichment tag in the peaks from enriched samples. Typical tag fragmentations of the Cyhn-conjugated reduced sugar were detected at m/z 255.09, 240.08 and 223.05 in both IRMPD and EID spectra (FIGS. 13D and 13E). These fragment ions can be attributed to labile amide and hydrazide bond fragmentations providing diagnostic ions to identify the enriched glycans and differentiate them from other molecules. In CID we were unable to observe the tag fragment ions due to the low-mass cutoff (LMCO) of the ion trap, also known as the one-third rule, in which product ions with masses below 28% of the precursor ions mass cannot be trapped during CID.

Based on the applied methods, the EID spectra resulted in the most fragmentation compared to CID and IRMPD. Cross-ring fragmentations (i.e. $^{1,5}$X ions) were more abundant along with the common glycosidic cleavages (Y and Z ions). Upon CID and IRMPD, the sugar at the third position from the reducing end gave a mass of 217 Da, 14 Da higher than a hexosamine sugar. While CID and IRMPD did not provide more information to characterize this sugar, the EID spectra of fOS$_{Cc}$ (FIG. 13E) contained a fragment ion at m/z 841.3412 that is consistent with the loss of 43.9888 Da from the Z$_3$ ion (m/z 885.3300). This appears to be the loss of a CO$_2$ (theoretical mass 43.9898), which supports the presence of N-acetyl hexuronic acid (HexNAcA) moiety at this third position. Taken together, based on this evidence the fOS$_{Cc}$ structure is predicted to be a branched HexNAc-[Hex]-HexNAc-HexNAcA-HexNAc-diNAcBac.

This result is different from the molecular structure of fOS$_{Cc}$ previously reported based on chromatographic purification followed by MS and NMR analyses, where the fOS$_{Cc}$ is assigned to be a Glc4RLac-GalNAc-[Glc]-GalNAc-GalNAc-GalNAc-diNAcBac (Nothaft et al. (2012) Mol. Cell. Proteomics 11:1203-1219) with a glucolactilic acid (Glc4RLac) at the non-reducing end. But our result agrees well with the finding from Jervis et al. (Jervis et al., (2012) J. Bacteriol. 194:2355-2362). Based on the pgl operon of C. concisus, we assumed that the fOS$_{Cc}$ would be composed of GalNAc units as well as diNAcBac like fOS$_{Cj}$. High-resolution MS/MS analysis revealed that the third sugar from the reducing end contains a carboxylic acid moiety like N-acetyl galacturonic acid (GalNacA), previously identified in LPS O-antigen structure of Aeromonas salmonicida 80204-1 strain (Wang et al., (2004), Eur. J. Biochem. 271:4507-4516), so the more likely structure of fOS$_{Cc}$ is GalNAc-[Glc]-GalNAc-GalNAc-GalNacA-GalNAc-diNAcBac.

A Linear fOS in Desulfovibrionales

Figure 14A:
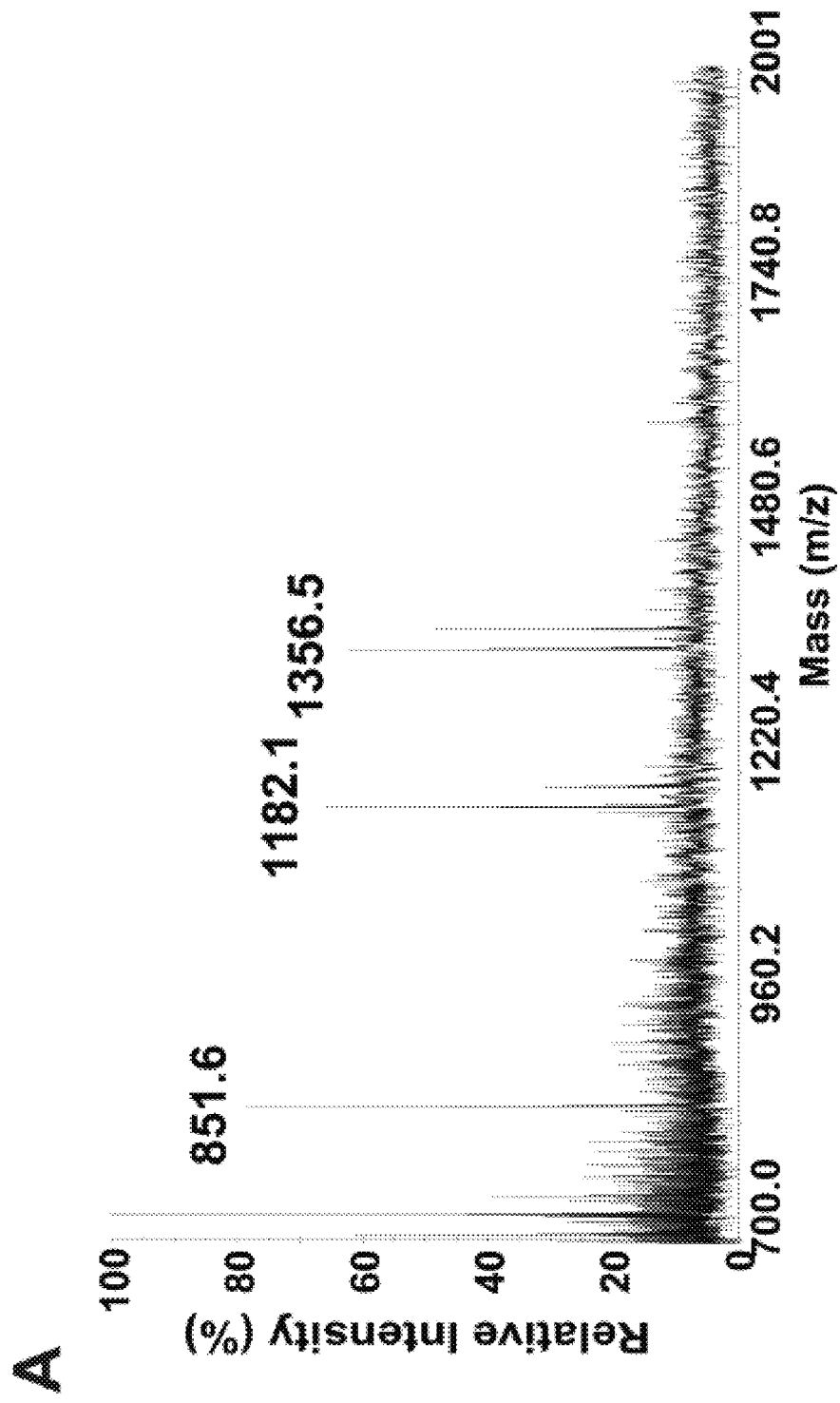
FIG. 14A shows the MALDI-TOF MS spectrum of enriched fOS$_{Dd}$. The enrichment was performed with periplasmic extracts from *D. desulfuricans* by solid-phase extraction.
Figure 14B:
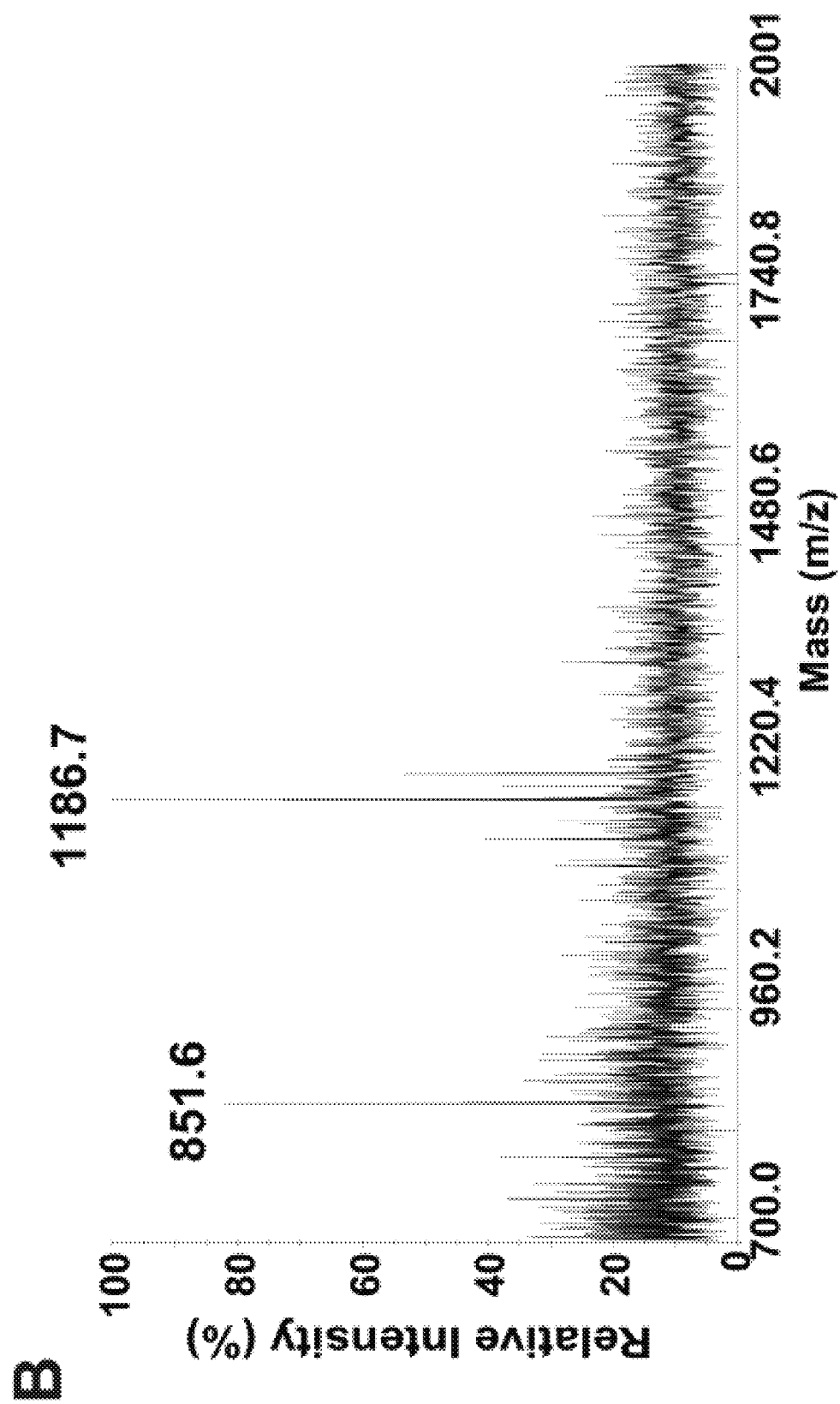
FIG. 14B shows the MALDI-TOF MS spectrum of enriched fOS$_{Dv}$. The enrichment was performed with periplasmic extracts from *D. vulgaris* by solid-phase extraction.
Figure 14C:
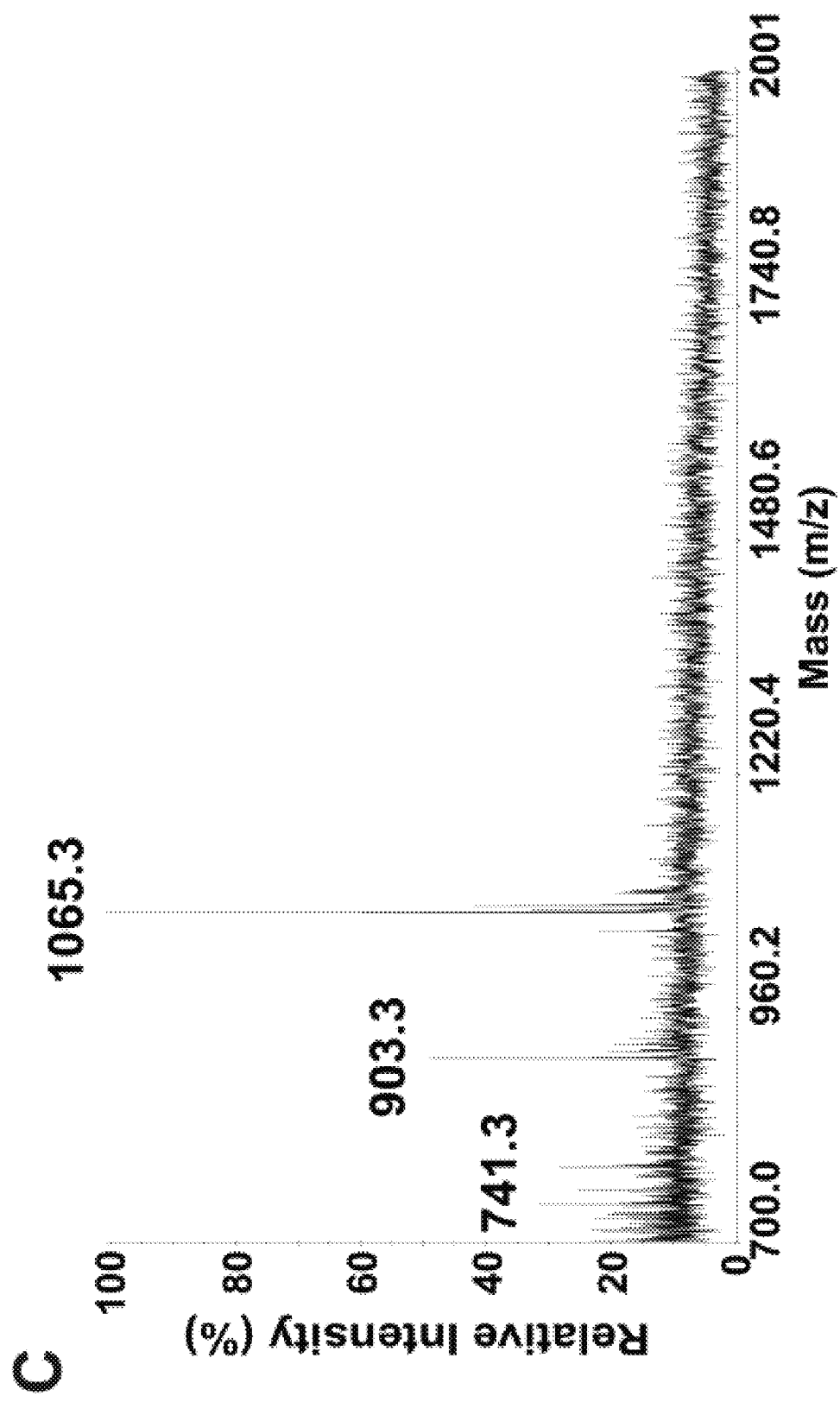
FIG. 14C shows the MALDI-TOF MS spectrum of enriched fOS$_{Dd}$. The enrichment was performed with periplasmic extracts from *D. desulfuricans* by the hydrazide-functionalized resins.
Figure 14D:
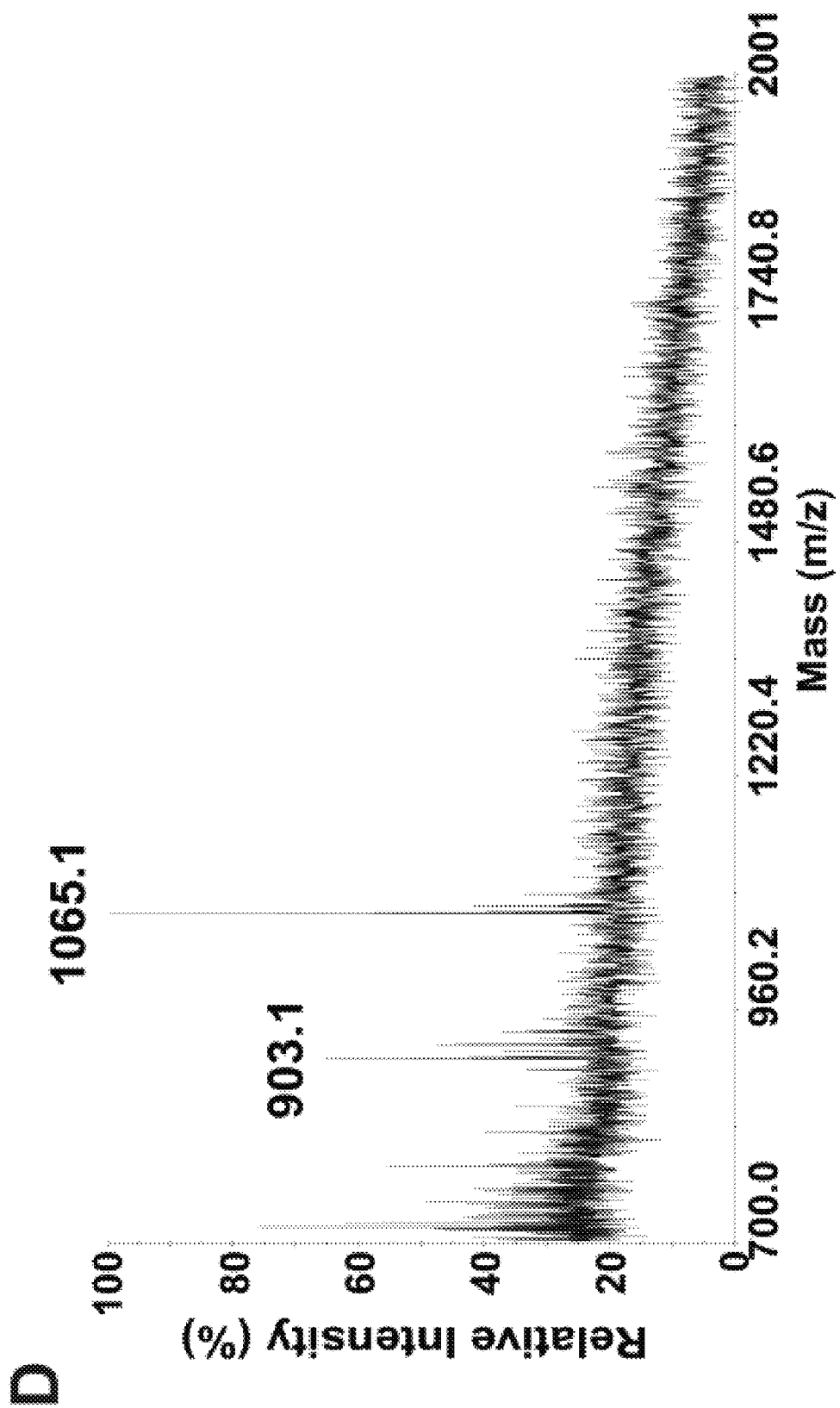
FIG. 14D shows the MALDI-TOF MS spectrum of enriched fOS$_{Dd}$. The enrichment was performed with periplasmic extracts from *D. vulgaris* by the hydrazide-functionalized resins.
Figure 14E:
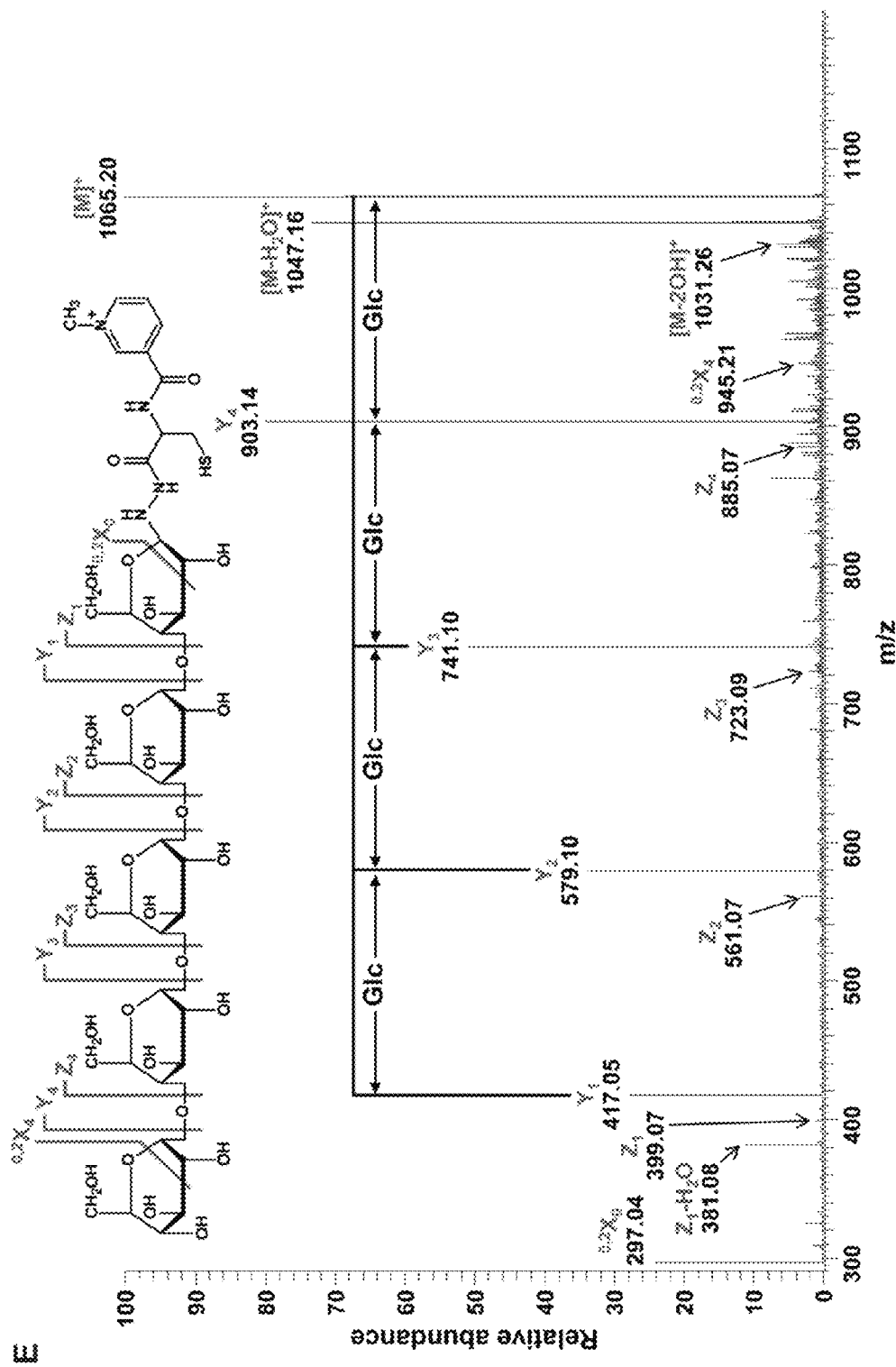
FIG. 14E shows the CID MS/MS spectrum of the fOS$_{Dd}$ from *D. desulfuricans* (CID 30-ms irradiation with 20% collision energy).
Figure 14F:
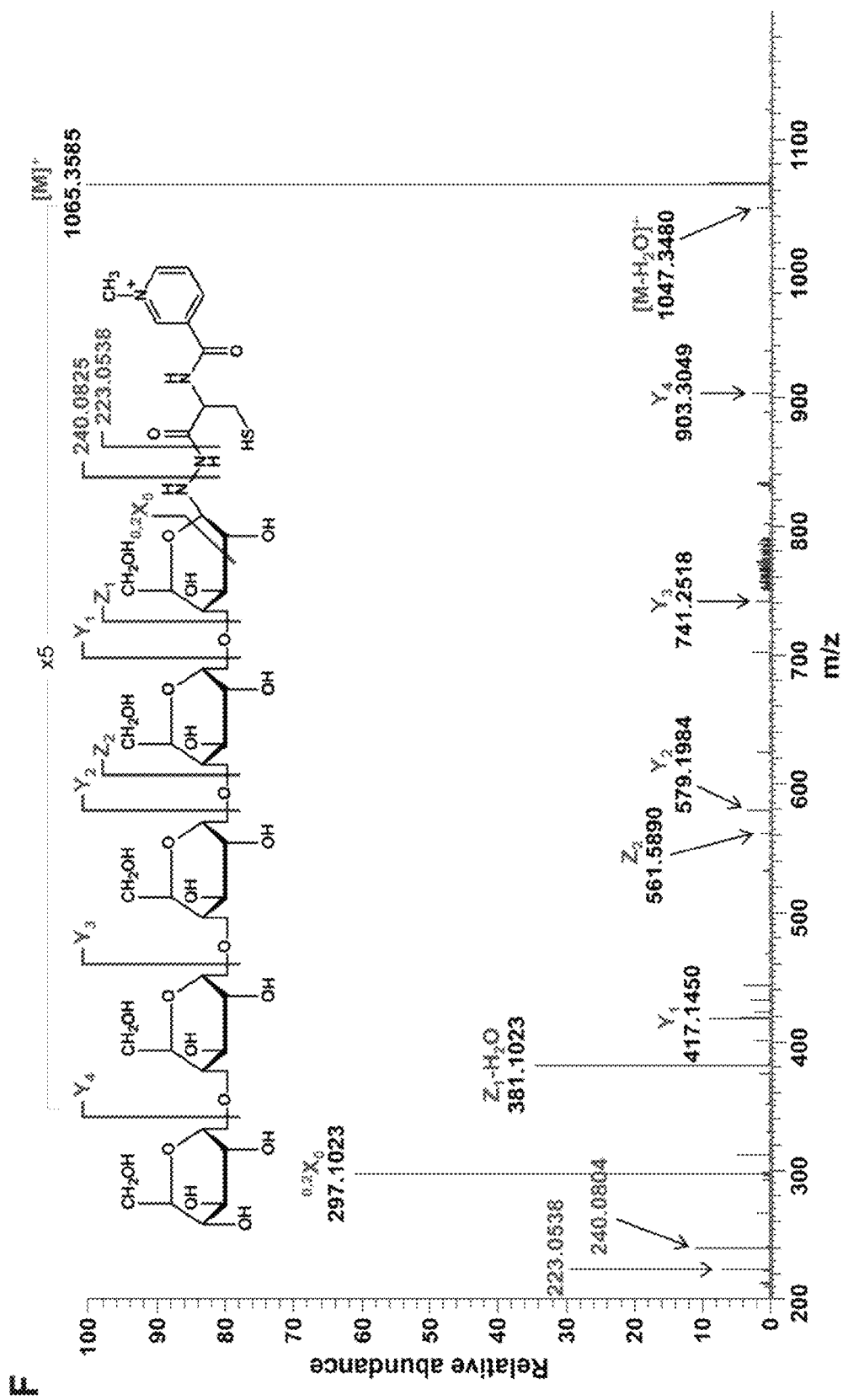
FIG. 14F shows the IRMPD MS/MS spectrum of the fOS$_{Dd}$ from *D. desulfuricans* (IRMPD 50-ms with 20-W laser power).
Figure 14G:
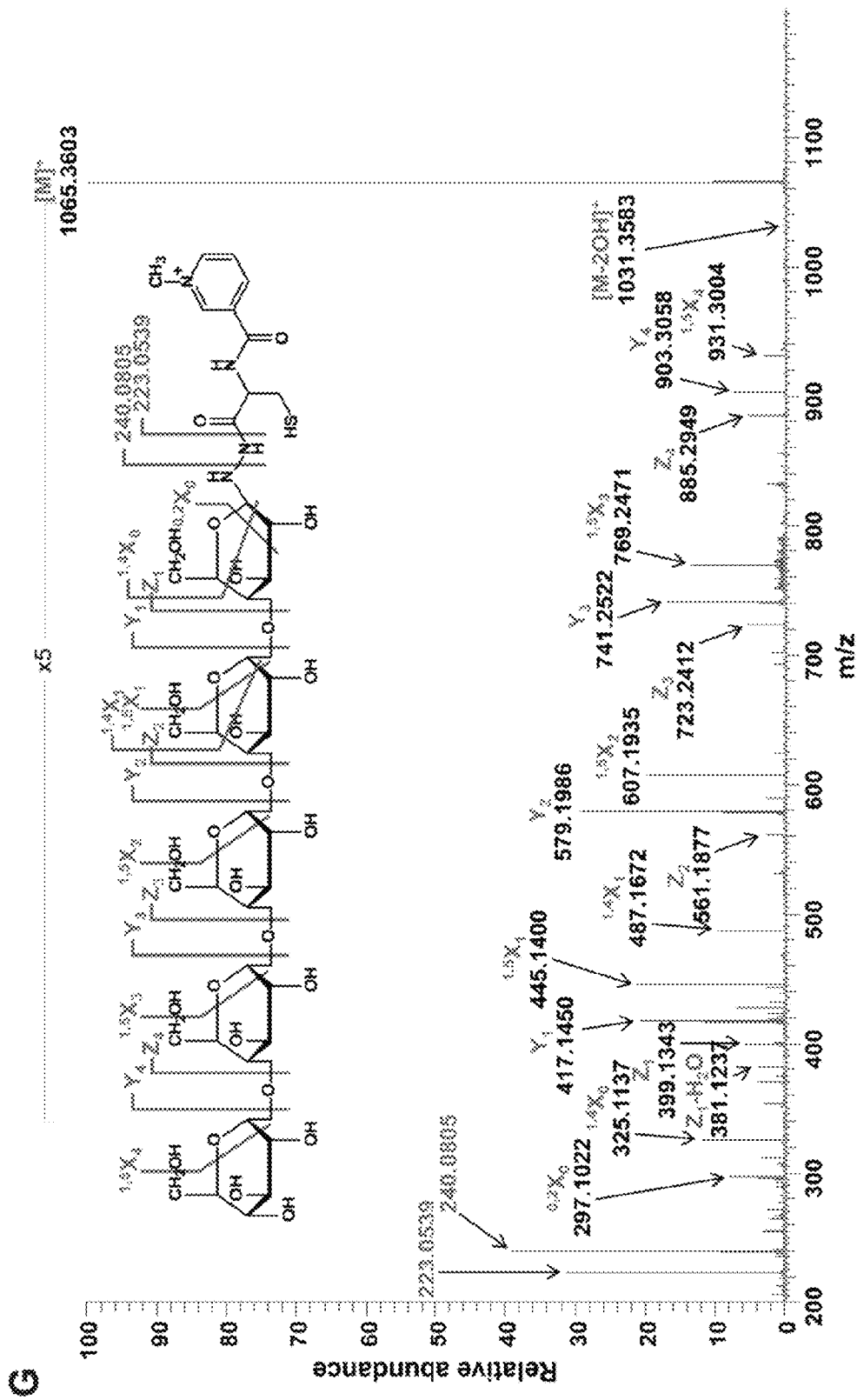
FIG. 14G shows the EID MS/MS spectrum of the fOS$_{Dd}$ from *D. desulfuricans* (EID 70-ms with a voltage of −25 V).
Figure 15:
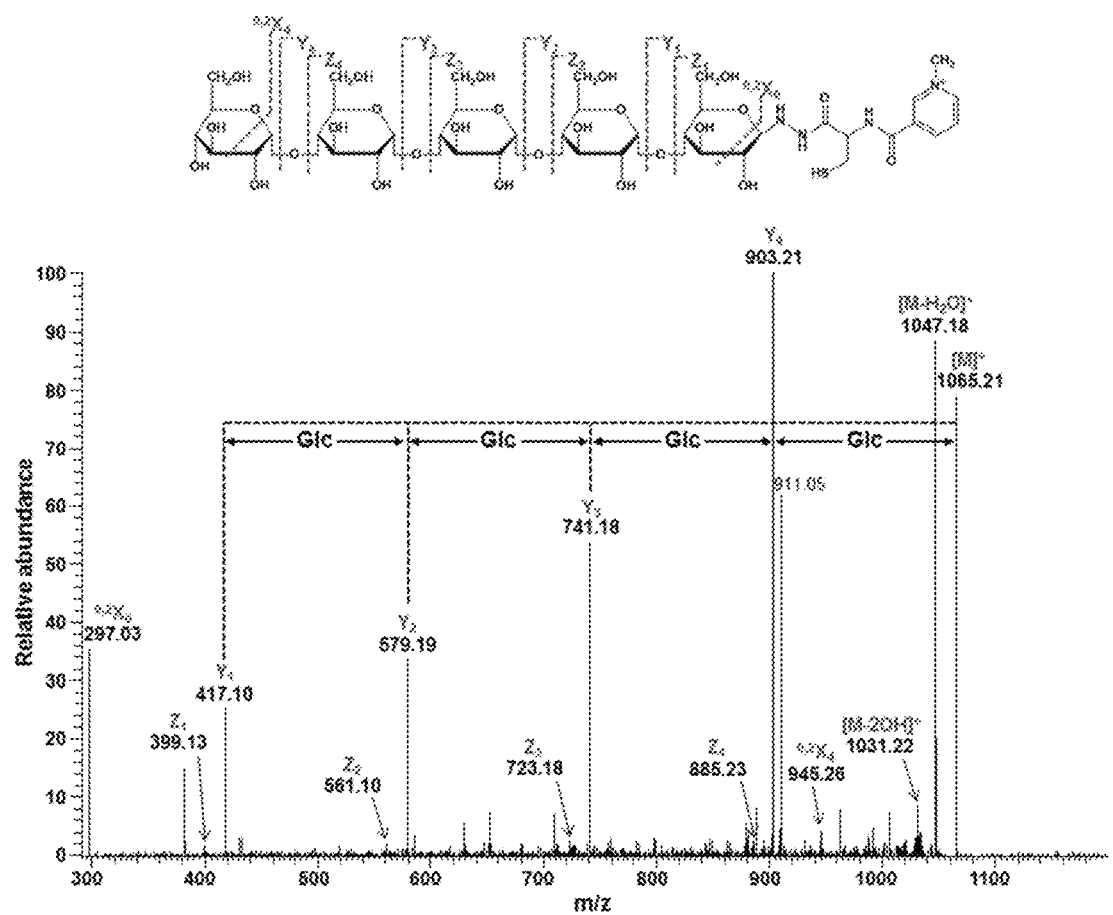
FIG. 15 shows the CID MS/MS spectrum of enriched fOS$_{Dv}$.
Figure 16:
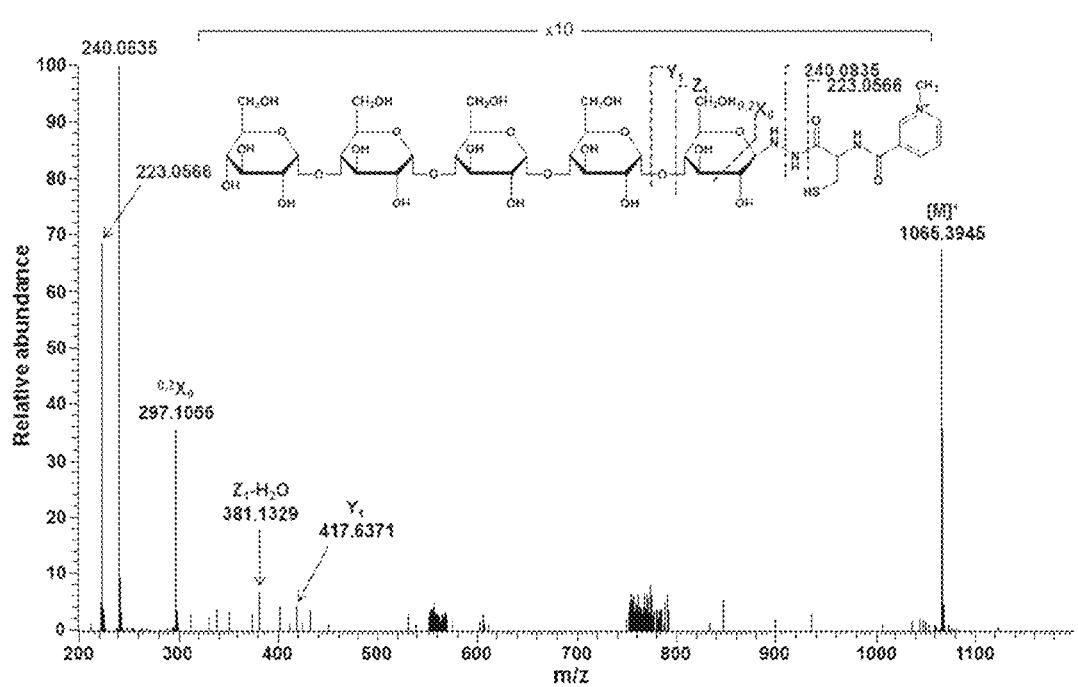
FIG. 16 shows the IRMPD MS/MS spectrum of enriched fOS$_{Dv}$.
Figure 17:
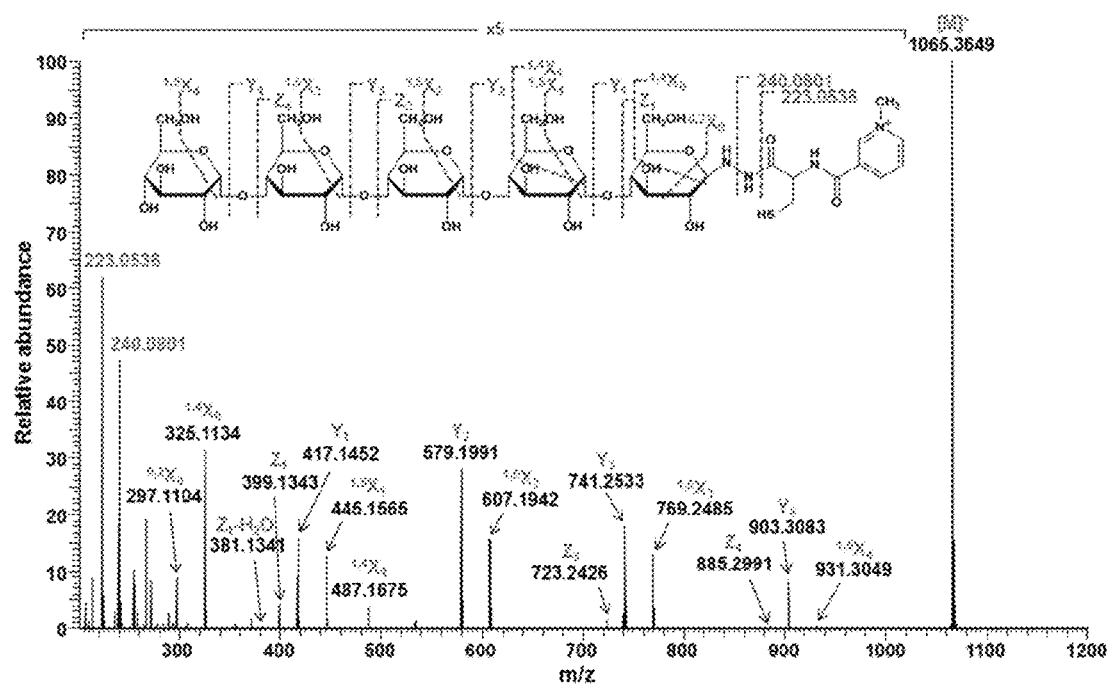
FIG. 17 shows the EID MS/MS spectrum of enriched fOS$_{Dv}$.

Solid phase extraction of Desulfovibrio species resulted in a number of large peaks by MS suggestive of multiple fOSs (FIGS. 14A and 14B); however, upon hydrazide-enrichment, selective for glycans, the larger peaks could be ruled out (i.e. m/z 1182.1, 1186.7 and 1356.5). The remaining peaks corresponded to a series from tri- to penta-hexoses in the enriched samples of D. desulfuricans and D. vulgaris (FIGS. 14C and 14D). To clarify the structures of the uncharacterized fOS, the predominant peak at m/z 1065.3603 was subjected to MS/MS analysis, as performed for the C. concisus fOS. The MS/MS spectra obtained from the precursor ion at m/z 1065.36 of both samples were identical to each other (FIGS. 14E, 14F, 14G and 15-17). The monosaccharide composition of the peak at m/z 1065.36 was predicted to be a penta-hexose by a series of Y and Z ions shown in CID spectra (FIGS. 14E and 15). The Cyhn conjugation was confirmed by the diagnostic fragment ions (i.e. m/z 240.0804 and 223.0538) in IRMPD spectra (FIG. 14F). As shown in FIG. 14G, in EID spectra, $^{1,4}$X and $^{1,5}$X ring cleavage ions were observed. The reducing end hexose from fOS$_{Dd}$ and fOS$_{Dv}$ was discriminated from the diNAcBac in fOS$_{Cj}$ and fOS$_{Cc}$ by $^{0,2}X_0$ fragment ions at m/z 297.1022.

Figure 18:
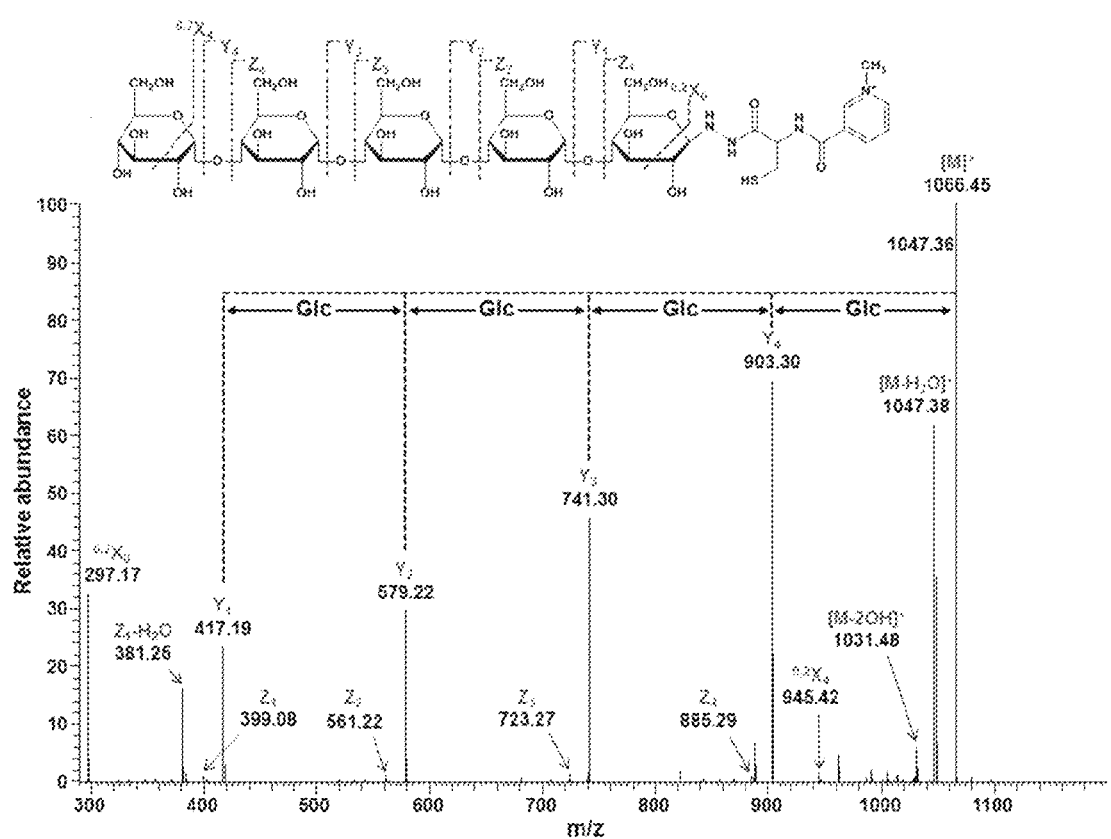
FIG. 18 shows the CID MS/MS spectrum of maltopentaose.
Figure 19:
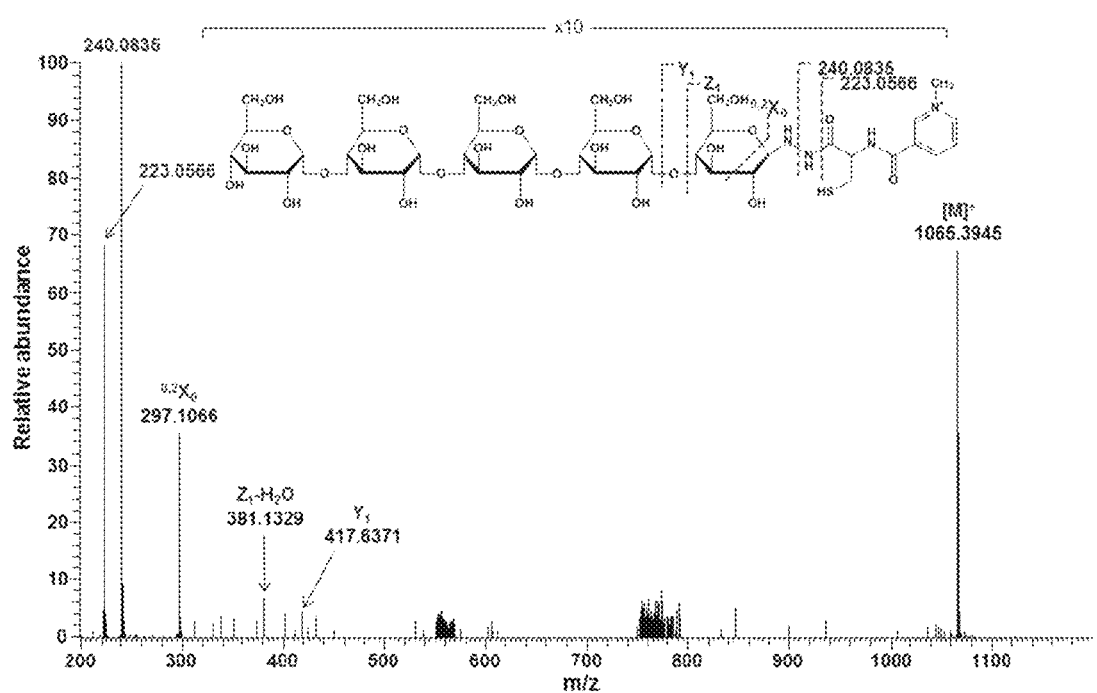
FIG. 19 shows the IRMPD MS/MS spectrum of maltopentaose.
Figure 20:
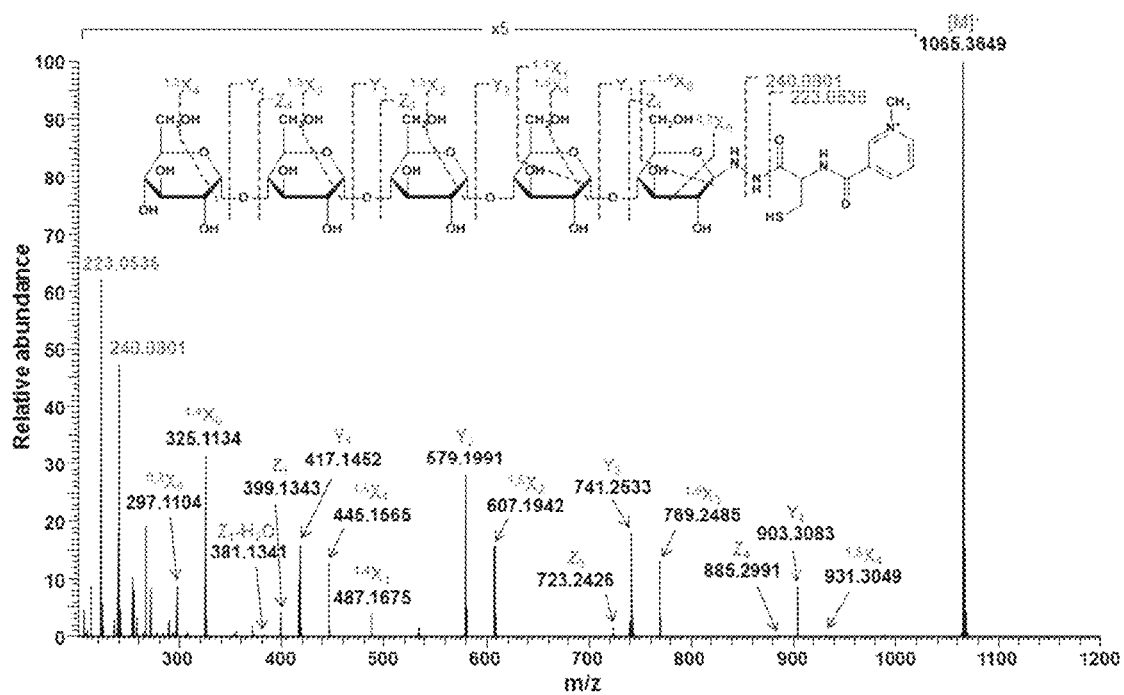
FIG. 20 shows the EID MS/MS spectrum of maltopentaose.

Based on the complementary analysis of the tandem MS spectra of these samples, the molecule at m/z 1065.36 was proposed to be a linear pentasaccharide. More likely this molecule corresponds to a maltopentaose [Glcα(1,4)Glcα (1,4)Glcα(1,4)Glcα(1,4)Glc], a linear oligosaccharide with five α1→4 linked glucose units, because the MS/MS spectra of the peak at m/z 1065.3603 were identical with those of the Cyhn-conjugated maltopentaose, used for control experiments in this study (FIGS. 18, 19 and 20), but this does not rule out other possible isomers, such as galactose as there are predicted UDP-glucose 4-epimerase gene orthologs responsible for supply of UDP-galactose.

As demonstrated above, we identified linear oligohexose units from periplasmic extracts of Desulfovibrionales. Interestingly, the fOS profiles from *D. desulfuricans* G20 and *D. vulgaris* Hildenborough were identical even though their predicted pgl operons were different. Predicted pgl genes in *Desulfovibrio* were identified by sequence similarity to *C. jejuni* genes, therefore some genes NLG genes may have been missed. Likely, some of the predicted pgl genes may not be involved in the NLG pathway, but instead be associated with biosynthesis of other glycoconjugates.

When the *C. jejuni* PglB is expressed in *E. coli*, multiple LLO species can be transferred to a protein suggesting the involvement of an *E. coli* multifunctional flippase (Valderrama-Rincon et al. (2012) *Nat. Chem. Biol.* 8, 434-436; Feldman et al. (2005) *Proc Natl Acad Sci USA* 102, 3026-3021). This is similar to what is seen in the *Desulfovibrio* species where multiple fOS in the periplasm suggest the LLO flippase can catalyze the transfer of multiple LLOs. It is unclear what the role of this broader activity may be in *Desulfovibrio* species. It is clear that *D. desulfuricans* PglB can catalyze the transfer of non-native oligosaccharides in heterologous systems (Ielmini et al. (2011) *Glycobiology* 21, 734-742) suggesting that the N-linked glycan in these species can be heterogeneous. The results are also consistent with the crystal structure of a glycosylated protein from *D. gigas* where a pair of hexoses is compatible with the electron density (PDBID 1Z1N) (Santos-Silva et al., (2007) *J Mol Biol* 370, 659-673). While the authors predicted N-acetylhexosamines due to a measured glycan mass of +613 Da, this is inconsistent with three of these moieties (+609 Da). Therefore, the nature of the glycan in *D. gigas* remains to be determined.

The work presented here provides new insight into bacterial N-linked glycosylation. We demonstrate a robust method for fOS purification that additionally provides a convenient signature ion for MS characterization. The use of diverse fragmentation techniques provides a rapid tool for accurately characterizing the individual glycan moieties. It provides a significant improvement over traditional CID without the need for costly NMR studies. The identification periplasmic fOS in *Desulfovibrio* species provides stronger evidence for the presence of NLG system species beyond ε-proteobacteria. For *D. desulfuricans* and *D. vulgaris*, this work suggests a distinct NLG pathway with broader substrate specificity. Coupled with a simpler sequon requirement relative to ε-proteobacteria (Santos-Silva et al., (2007) *J Mol Biol* 370, 659-673), this suggests that Desulfovibrionales glycosyltransferases may provide useful tools for glycoengineering. Clearly, there is more work to understand the diversity of bacterial oligosaccharides.

Chemicals and Materials.

All reagents and solvents were purchased from commercial vendors and used as received. Proton chemical shifts are reported in parts per million (ppm; δ) relative to CDCl$_3$ solvent ($^1$H δ=7.26). NMR data are reported as follows: chemical shifts, multiplicity (obs=obscured, app=apparent, br=broad, s=singlet, d=doublet, t=triplet, q=quartet, m=multiplet); coupling constant(s) in Hz; integration. Unless otherwise indicated, NMR data were collected at 25° C. Nicotinic acid, N,N-dimethylformamide, N,N-diisopropylethylamine, L-cysteine methyl ester hydrochloride, hydrazine monohydrate, sodium meta-periodate, and iodomethane were purchased from Sigma-Aldrich (St. Louis, Mo.). Thionyl chloride was obtained from Junsei Chemical Co., Ltd (Tokyo, Japan). N-hydroxysuccinimide (NHS)-fluorescein was obtained from Thermo Fisher Scientific Inc. (Waltham, Mass.). Thiopropyl Sepharose™ 6B resins and BcMag™ thiol-activated magnetic beads were purchased from GE Healthcare Biosciences (Pittsburgh, Pa.) and Bioclone Inc. (San Diego, Calif.), respectively. All other chemicals were of analytical grade.

Chemical Syntheses of Cationic Cysteine Hydrazide Derivative.

Step 1 for cysteine methyl ester nicotinamide 4. Nicotinic acid (2, 7.9 g, 64.2 mmol) was suspended in 100 mL thionyl chloride (512 mmol). N,N-Dimethylformamide (0.2 mL, 2.6 mmol) was added to the solution as a catalyst. The reaction mixture was stirred for 1 h at room temperature (RT), during which time the slurry became homogeneous. Upon complete consumption of the nicotinic acid, the thionyl chloride was removed in vacuo, and the residue was azeotroped with benzene to remove residual thionyl chloride and HCl. The crude off-white solid (3) was suspended in 150 mL of acetonitrile and cooled to 0° C. under a nitrogen atmosphere. A heterogeneous mixture containing cysteine methyl ester hydrochloride 1 (10 g, 58.3 mmol) and N,N-diisopropylethylamine (8.3 mL, 47.2 mmol) in 200 mL of acetonitrile was transferred in one portion to the nicotinic acid chloride. The resulting thick white slurry was stirred vigorously and allowed to warm to RT over 2 hours. The reaction was quenched with saturated aqueous NaHCO$_3$ and the acetonitrile was concentrated in vacuo. The aqueous phase was extracted with dichloromethane (3×100 mL), and the combined organic phases were washed with brine. The organic layer was dried over Na$_2$SO$_4$, and then the solvent was removed in vacuo. The crude residue was purified using silica column chromatography (50→100% EtOAc:hexanes) affording the cysteine methyl ester nicotinamide 4 as a viscous colorless oil (6.0 g, 25.0 mmol, 43% yield). $^1$H NMR (500 MHz, CDCl$_3$) δ: 9.07 (dd, J=2.3, 0.9 Hz, 1H), 8.77 (dd, J=4.9, 1.7 Hz, 1H), 8.15 (ddd, J=7.9, 2.3, 1.7 Hz, 1H), 7.42 (ddd, J=7.9, 4.9, 0.9 Hz, 1H), 7.09 (br d, J=7.1 Hz, 1H), 5.09 (dt, J=7.1, 4.0 Hz, 1H), 3.85 (s, 3H), 3.16 (dd, J=9.0, 4.0 Hz, 2H), 1.40 (t, J=9.0 Hz, 1H); $^{13}$C NMR (126 MHz, CDCl$_3$) δ: 170.37, 165.17, 152.69, 148.24, 135.06, 129.22, 123.46, 53.92, 53.02, 26.78; FTIR (NaCl, thin film) 3309, 3035, 2951, 1740, 1653, 1591, 1539, 1351, 1217 cm$^{-1}$; HRMS (ESI+) calc'd for C$_{10}$H$_{12}$N$_2$O$_3$S [M+H]$^+$ 241.0641, found 241.0643 (Supporting Information).

Step 2 for cystine dihydrazide nicotinamide 5. Cysteine methyl ester nicotinamide (4, 5.9 g, 24.4 mmol) was dissolved in 100 mL of dry methanol, then hydrazine monohydrate (9.5 mL, 195.2 mmol) was added. The solution was stirred at 50° C. for 5 hr, and the conversion to cysteine hydrazide nicotinamide (Cyhn monomer) was monitored by LC-MS. After the complete consumption of the staring material, the solution was sparged with oxygen gas for 15 minutes, then maintained under an oxygen atmosphere overnight at 50° C. After LC-MS analysis indicated complete conversion to the Cyhn disulfide dimer, the volatiles were removed in vacuo. The white residue was subjected to hot trituration in refluxing methanol (100 mL), and the precipitated product was filtered and washed with cold methanol. Drying under vacuum (0.1 Torr) afforded the cystine dihydrazide nicotinamide (Cyhn dimer) 5 as a white solid (2.4 g, 41% yield). $^1$H NMR (500 MHz, DMSO-$d_6$) δ: 9.42 (s, 1H), 8.99 (dd, J=2.3, 0.9 Hz, 1H), 8.87 (d, J=8.2 Hz, 1H), 8.69 (dd, J=4.8, 1.7 Hz, 1H), 8.17 (app dt, J=7.9, 2.0 Hz, 1H), 7.48 (ddd, J=7.9, 4.8, 0.9 Hz, 1H), 4.74 (m, 1H), 4.30 (br s, 2H), 3.22 (dd, J=13.6, 4.9 Hz, 1H), 3.03 (dd, J=13.6, 9.9 Hz, 1H); $^{13}$C NMR (126 MHz, DMSO-$d_6$) δ: 168.90, 165.04, 151.96, 148.72, 135.26, 129.44, 123.30, 51.34, 39.74; IR (NaCl/thin film) 3281, 3035, 2960, 1633, 1537, 1327; HRMS (ESI−) calc'd for $C_{18}H_{22}N_8O_4S_2$ [M−H]$^-$ 477.1133. found 477.1148 (Supporting Information).

Independent Preparation of Cyhn Monomer 6.

Cysteine methyl ester nicotinamide (4, 80 mg, 0.33 mmol) was dissolved in 400 mL of dry methanol under nitrogen, then hydrazine monohydrate (67 mL, 1.33 mmol) was added. The solution was stirred at RT until conversion to the cysteine hydrazide nicotinamide (Cyhn monomer) was achieved by LC-MS. All manipulations thereafter were performed under an argon atmostphere. The volatiles were concentrated in vacuo, and the residue was slurried in ethanol, filtered, and washed with cold ethanol. Drying under vacuum (0.1 Torr) afforded the cystine hydrazide nicotinamide (Cyhn monomer) as a white solid (50 mg, 62% yield). $^1$H NMR (500 MHz, DMSO-$d_6$) δ: 9.35 (s, 1H), 9.05 (dd, J=2.3, 0.9 Hz, 1H), 8.77 (d, J=8.1 Hz, 1H), 8.71 (dd, J=4.8, 1.7 Hz, 1H), 8.23 (app dt, J=7.9, 2.0 Hz, 1H), 7.52 (dd, J=8.0, 4.8 Hz, 1H), 4.51 (td, J=9.0, 5.2 Hz, 1H), 4.28 (br s, 2H), 2.90 (dd, J=13.5, 5.2 Hz, 1H), 2.82 (dd, J=13.5, 9.0 Hz, 1H), SH not observed; $^{13}$C NMR (126 MHz, DMSO-$d_6$) δ: 169.00, 165.17, 151.98, 148.76, 135.34, 129.55, 123.33, 55.10, 26.00. IR (NaCl/thin film) 3290, 3036, 2960, 1630, 1537, 1328; HRMS (ESI+) calc'd for $C_9H_{12}N_4O_2S$ [M+H]$^+$ 241.0754, found 241.0755 (Supporting Information).

Preparation of Cationic Cysteine Hydrazide-Functionalized Resins.

To hydrolyze the disulfide bond of the cysteine dihydrzide nicotinamide (Cyhn dimer), the Cyhn dimer (86 mg, 180 μmol) was suspended in 50% ethanol (1 mL), then one equivalent of dithiothreitol was added to the solution. Each thiopropyl Sepharose™ 6B resins (1 mL, 30 μmol) and BcMag™ thiol-activated magnetic beads (150 mg, 36 μmol) were washed with deionized water, respectively. The resins were suspended in 50% methanol. Five hundred milliliters of the Cyhn solution was added in each suspension. The suspensions were placed on rocking incubator at RT overnight. Then, the resins were washed with 50% methanol, followed by water and 20% ethanol. The resulting resins were stored in 20% ethanol at 4° C. prior to use.

Free Reducing Sugars were Enriched by Using Cationic Hydrazide Functionalized Resins for MS Analysis.

Figure 2A:
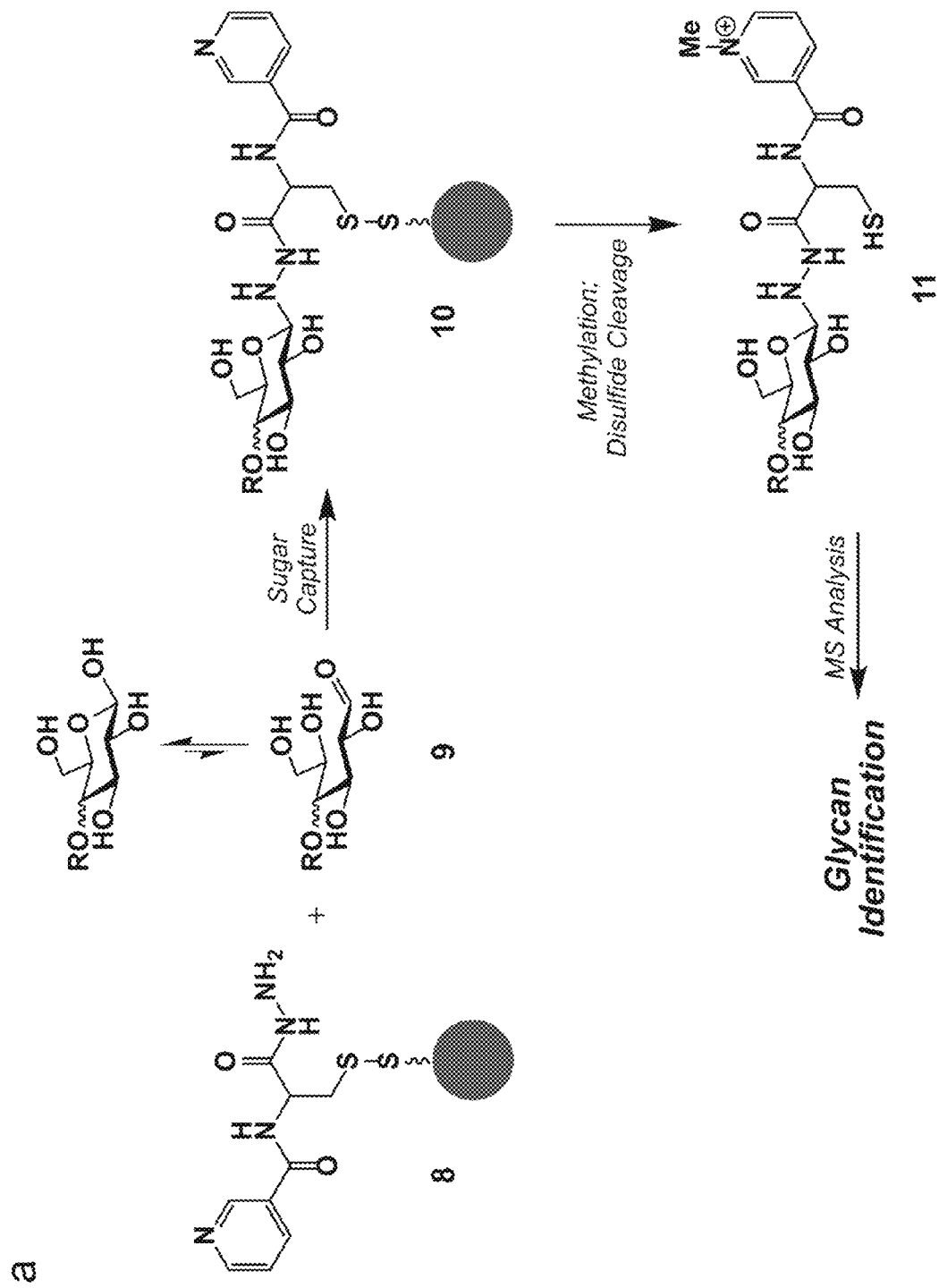
FIG. 2A shows a strategy for the selective capture and identification of bacterial glycans.
Figure 2B:
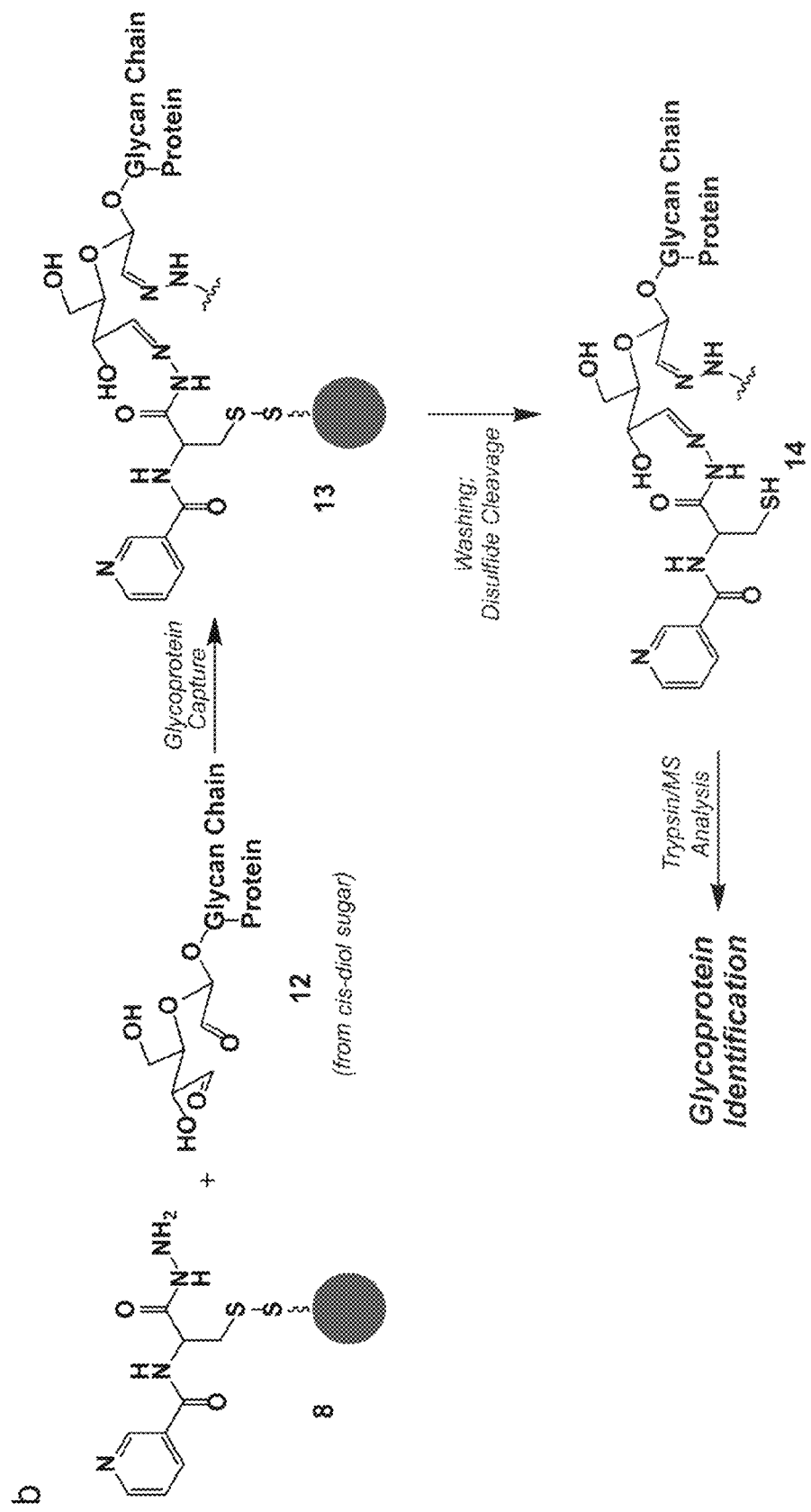
FIG. 2B shows a strategy for the selective capture and identification of glycoproteins.
Figure 3A:
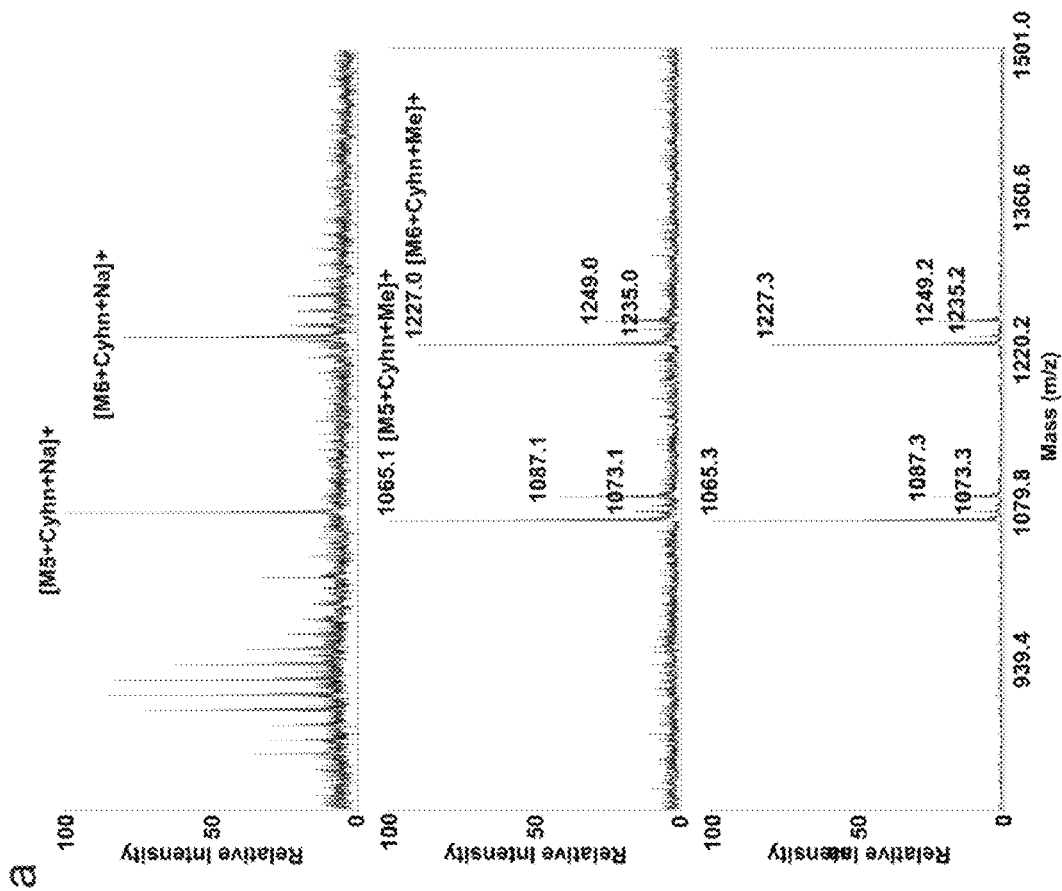
FIG. 3A shows methylation of maltopentaose (M5) and maltohexaose (M6) enriched Cyhn resins: upper panel, no methylation; middle panel, methylation with 20% iodomethane (MeI) in acetonitrile (ACN) at 50° C. for 2 h; lower panel, methylation with 20% MeI in ACN at 24° C. for 10 h.
Figure 3B:
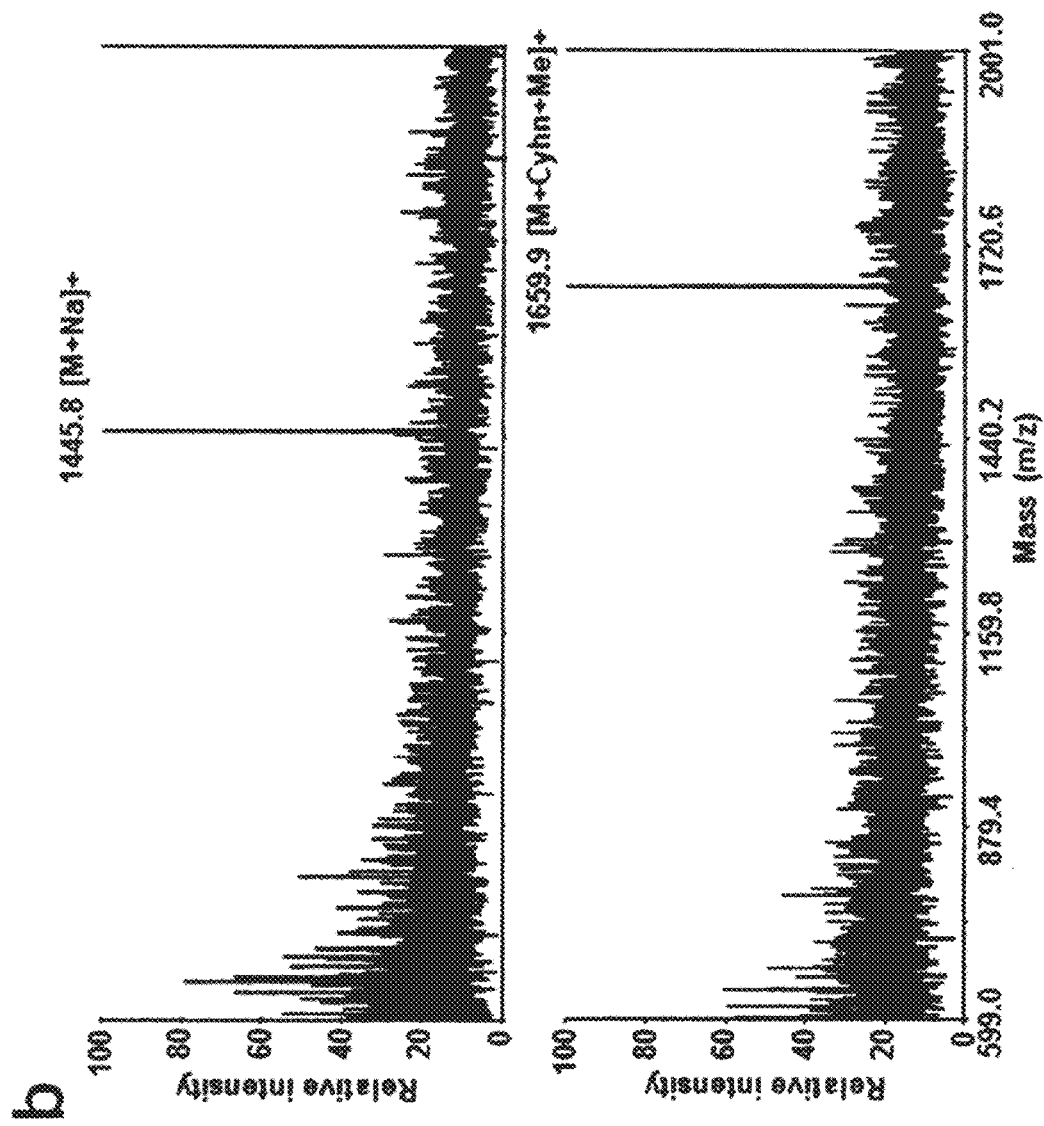
FIG. 3B shows methylation of Cyhn-conjugates and identification of free heptasaccharides from periplasmic extracts of C. jejuni.

The Cyhn resins were used to enrich soluble free sugars with reducing ends. The incubation of free oligosaccharides, i.e. commercially available maltopentaose (M5) and maltohexaose (M6), with the Cyhn-6B resins showed selective isolation of the reduced glycans; however, it was observed that the Cyhn-conjugated glycans ionized as the sodium adduct, not as the protonated pyridinium, although the pyridine ring of the Cyhn expected to be protonated in a solution of low pH. It was assumed that the glycan-Cyhn prefers sodium to proton due to the chelating effect of the hydroxyl groups of the glycans. Furthermore, we could not assume the pyridine of the Cyhn was readily protonated in gas phase during MS analysis. Rendering the Cyhn with a discrete positive charge via N-methylation of the pyridine nitrogen provided a solution (FIG. 2a). The mild post-methylation of the glycan-Cyhn conjugates allowed a permanent positive charge to the Cyhn conjugates, resulting in higher ionization signals during MS analysis (FIG. 3a). Finally, the Cyhn-enrichment followed by post-methylation was able to identify bacterial free heptasaccharide from periplasmic extracts of C. jejuni and compared with the non-enriched free glycans. As shown in FIG. 3b, the enriched free heptasaccharide showed greater ionization signals than other one.

Cationic Hydrazide Functionalized Resins Showed Selective Capture of Bacterial Glycoproteins.

Figure 4:
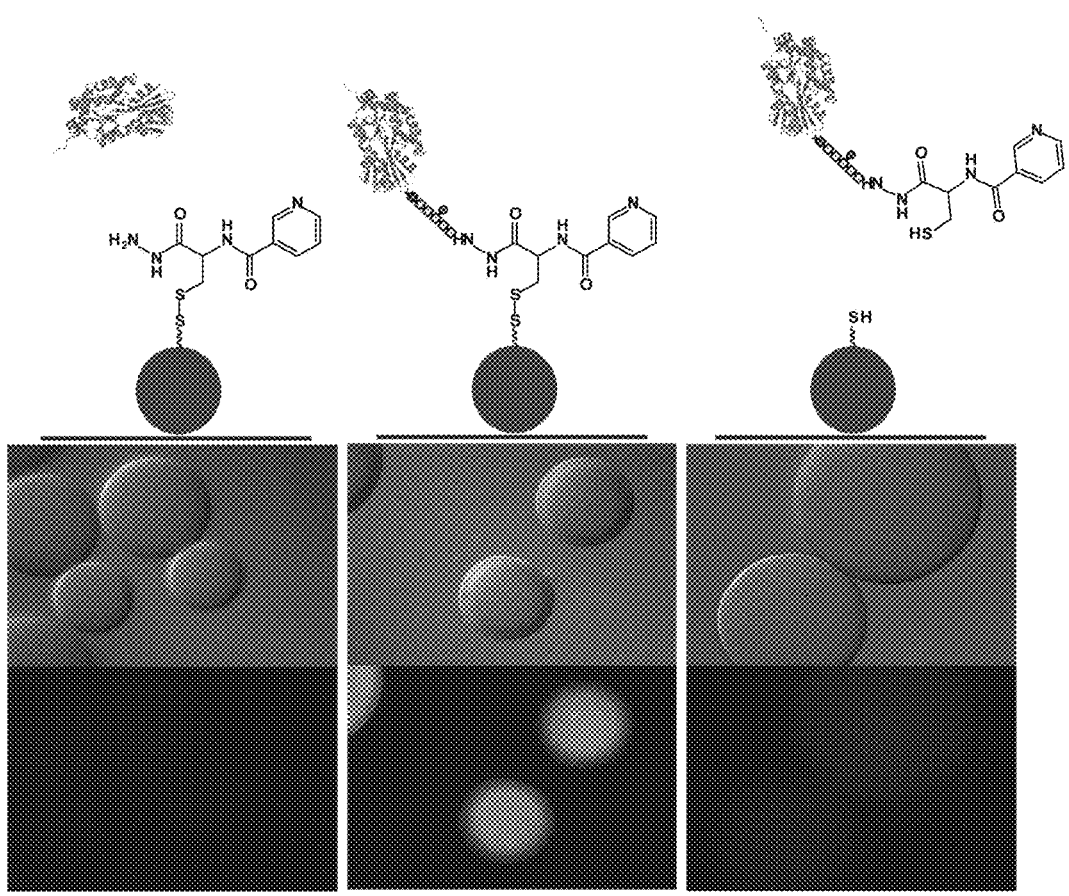
FIG. 4 shows selective enrichment of bacterial glycoproteins. Cyhn-6B resins were incubated with fluorescein-labeled oxidized MBP glycoproteins (middle) as well as fluorescenin-MBP without glycans (left), being scanned by fluorescence microscope. The fluorescence of the resin was also scanned after the reduction with dithiothreitol (right).
Figure 5:
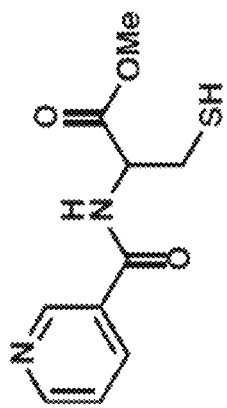
FIG. 5 shows the $^1$H NMR spectrum of compound 4.
Figure 5:
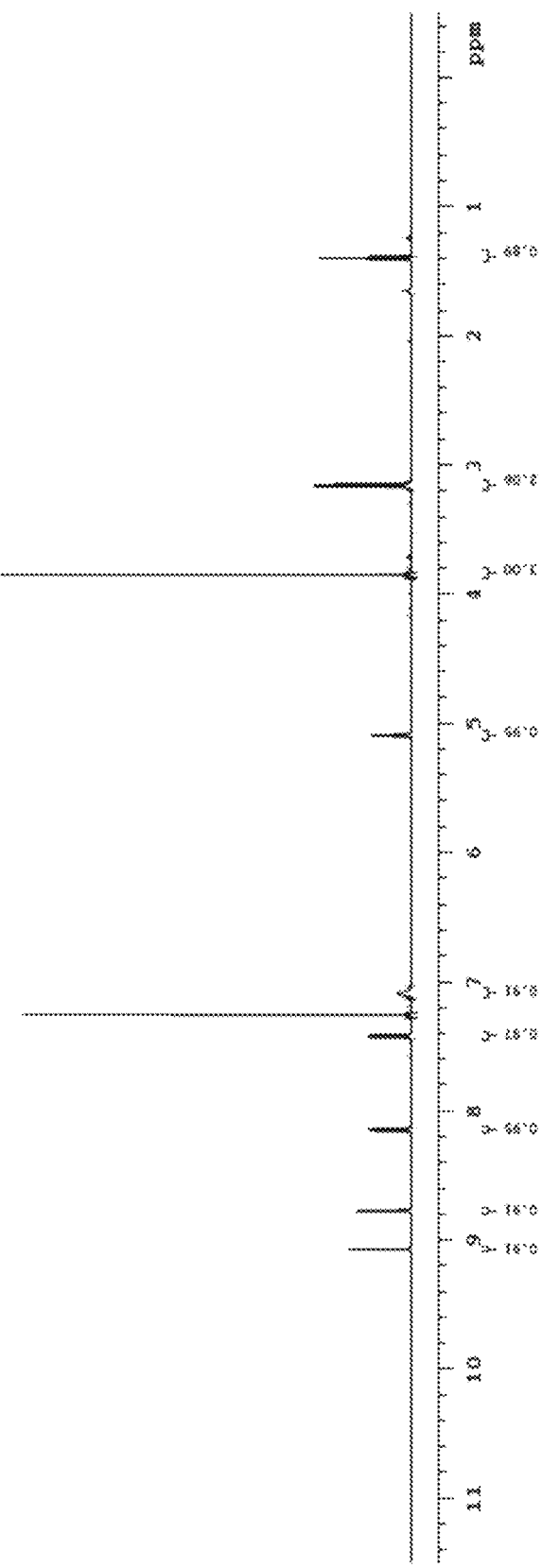
Figure 6:
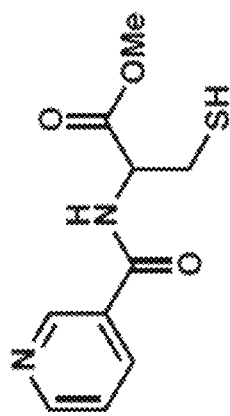
FIG. 6 shows the $^{13}$C NMR spectrum of compound 4.
Figure 6:
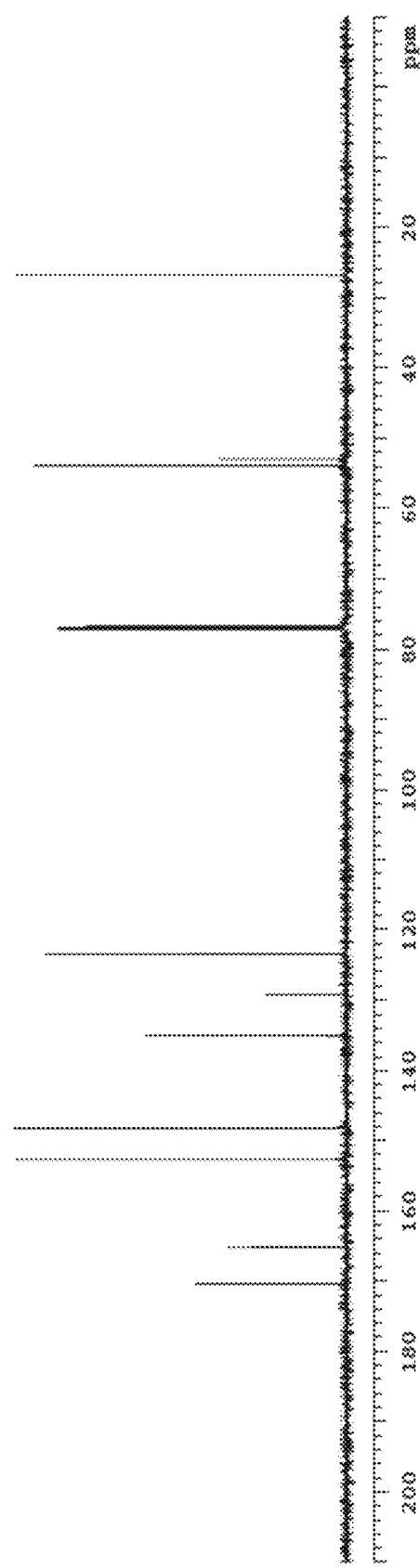
Figure 7:
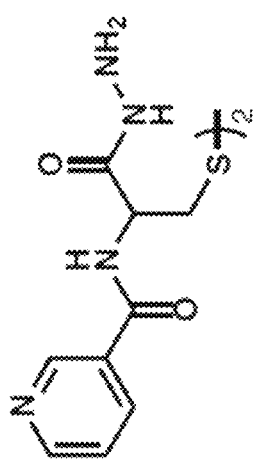
FIG. 7 shows the $^1$H NMR spectrum of compound 5.
Figure 7:
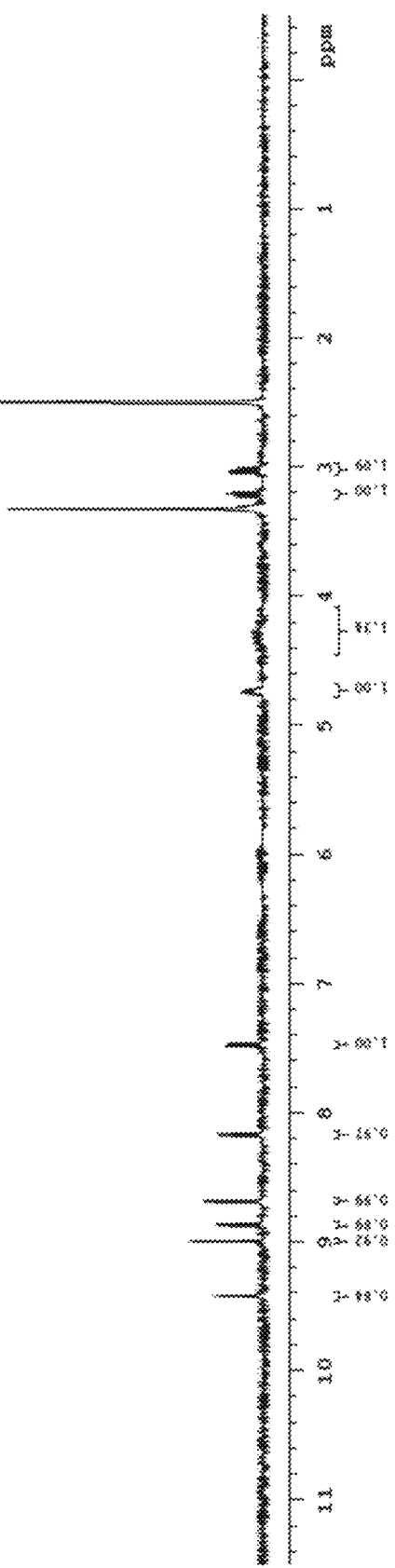
Figure 8:
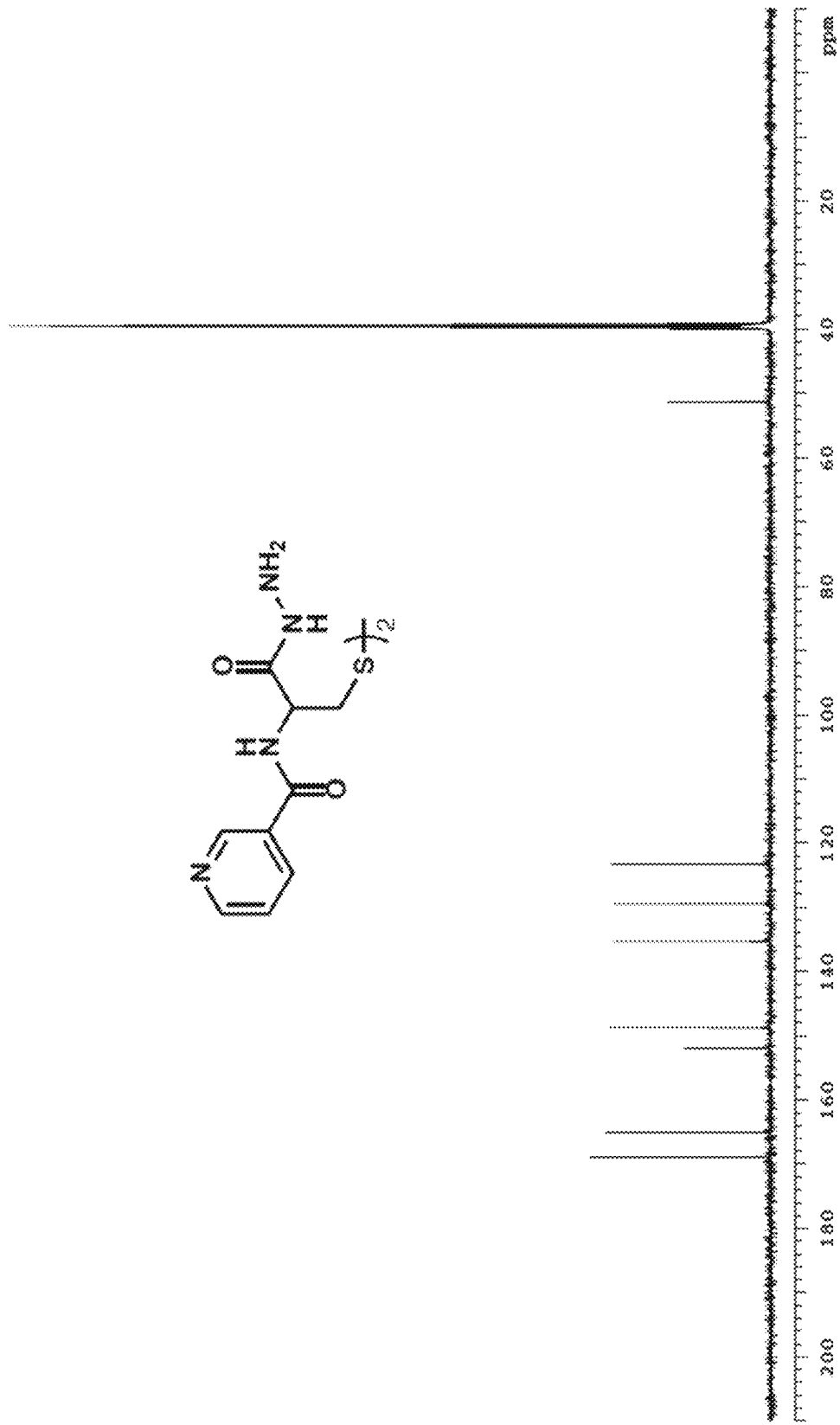
FIG. 8 shows the $^{13}$C NMR spectrum of compound 5.
Figure 9:
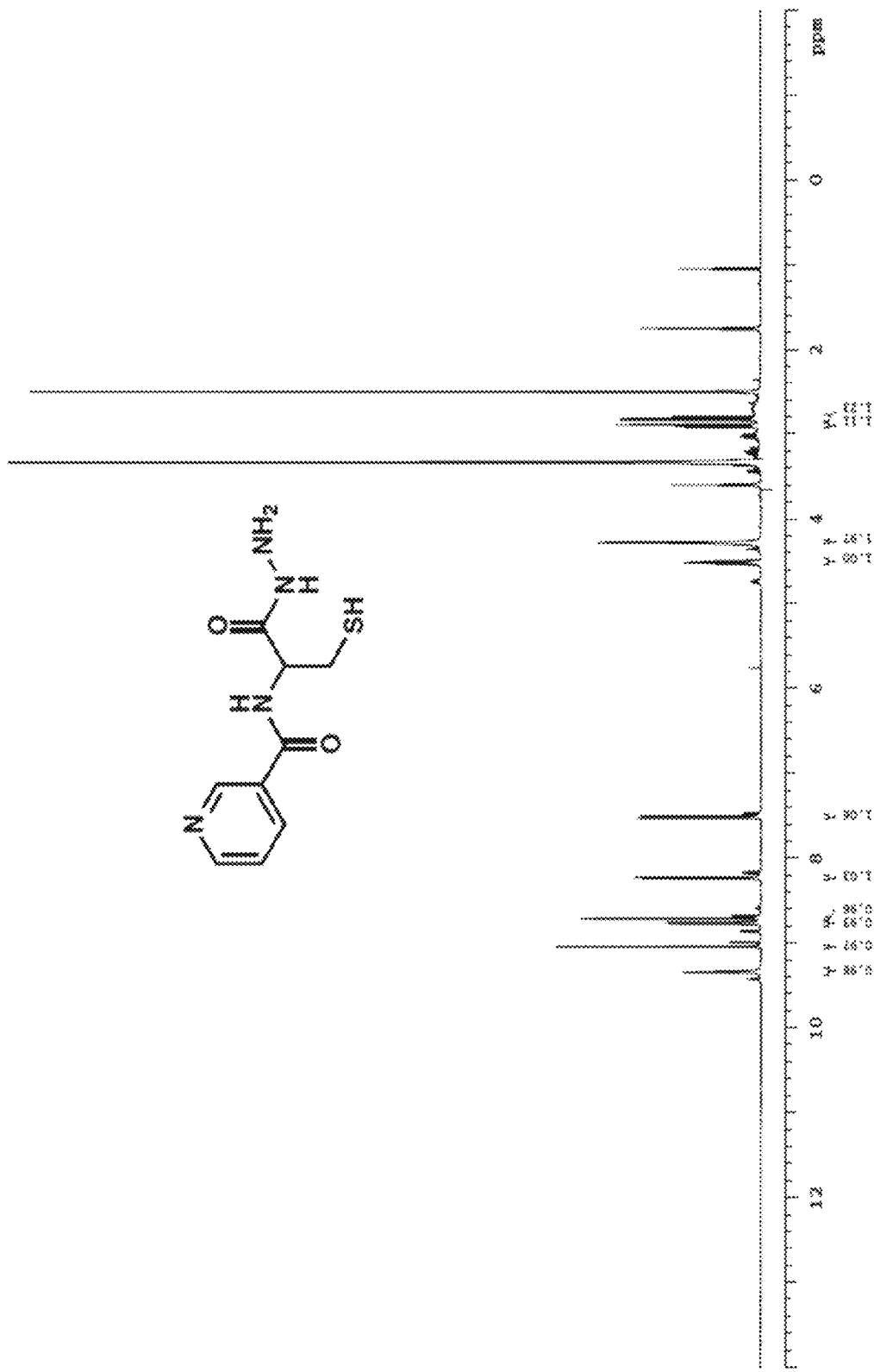
FIG. 9 shows the $^1$H NMR spectrum of compound 6.
Figure 10:
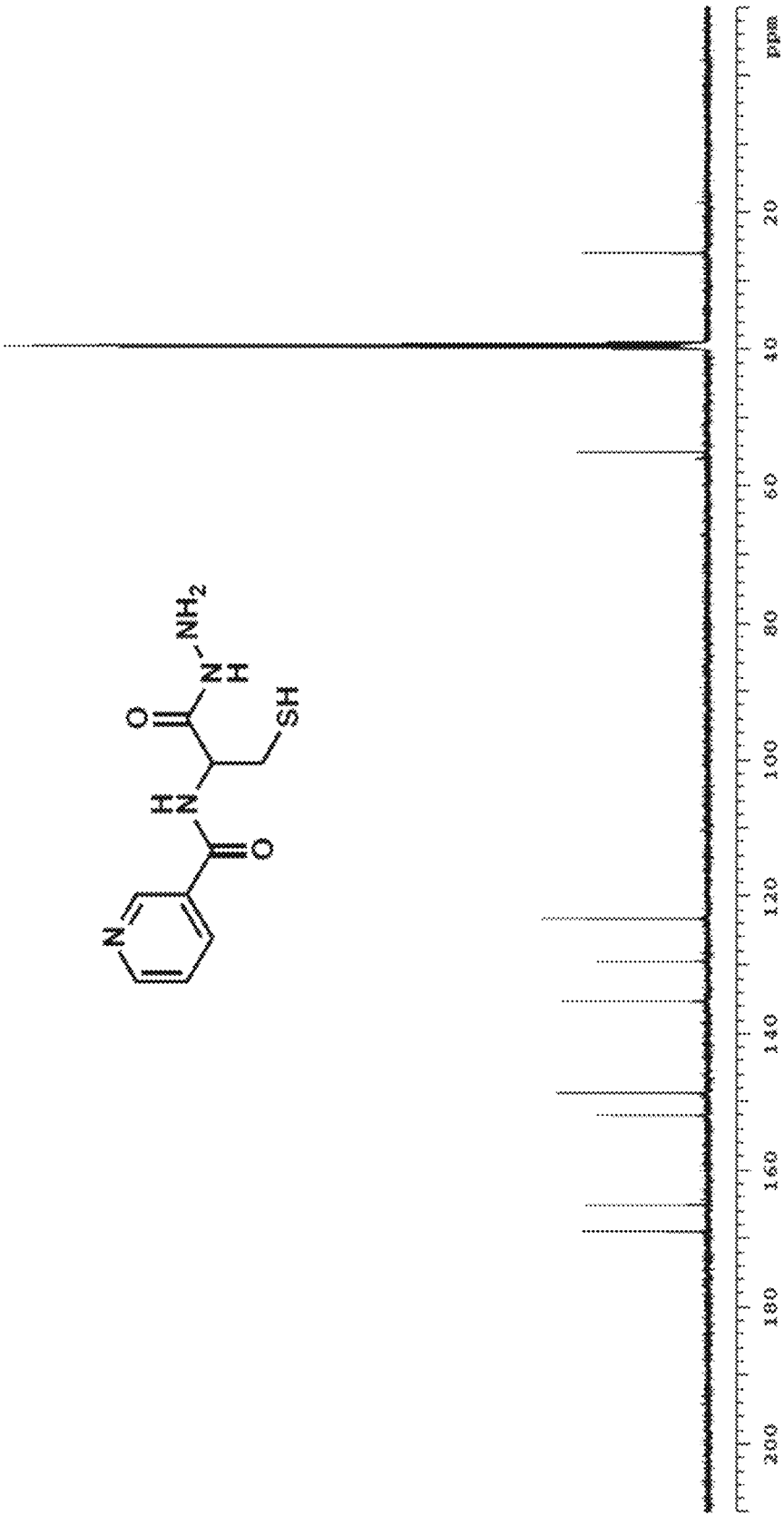
FIG. 10 shows the $^{13}$C NMR spectrum of compound 6.
Figure 11A:
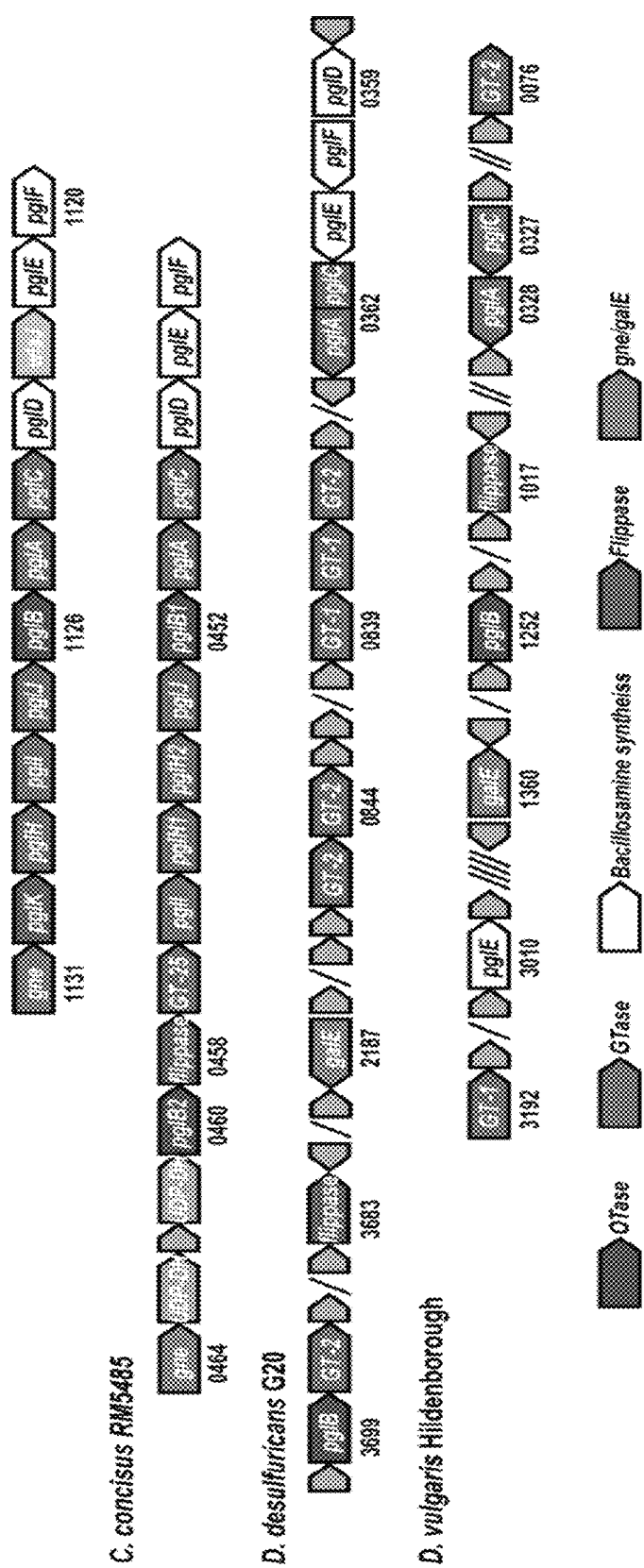
FIG. 11A shows selected bacterial protein N-glycosylation (pgl) gene clusters. Homologous pgl genes are scattered in the genomes of D. desulfuricans G20 and D. vulgaris Hildenborough, whereas those pgl genes are highly clustered in C. jejuni NCTC11168 and C. concisus RM5485. Blue, oligosaccharyltransferase gene (pglB); red, flippase gene (pglK); green, glycosyltransferase (GT) gene; purple, UDP-sugar epimerase gene (gne or galE); white, sugar biosynthesis gene. GT-1, group 1 family glycosyltransferase; GT-2, group 2 family glycosyltransferase; UDP-DH, UDP-sugar dehydrogenease. The predicted pgl genes in Desulfovibrio species were found by sequence similarity of C. jejuni pgl genes, so there might be some GT genes missing.
Figure 11B:
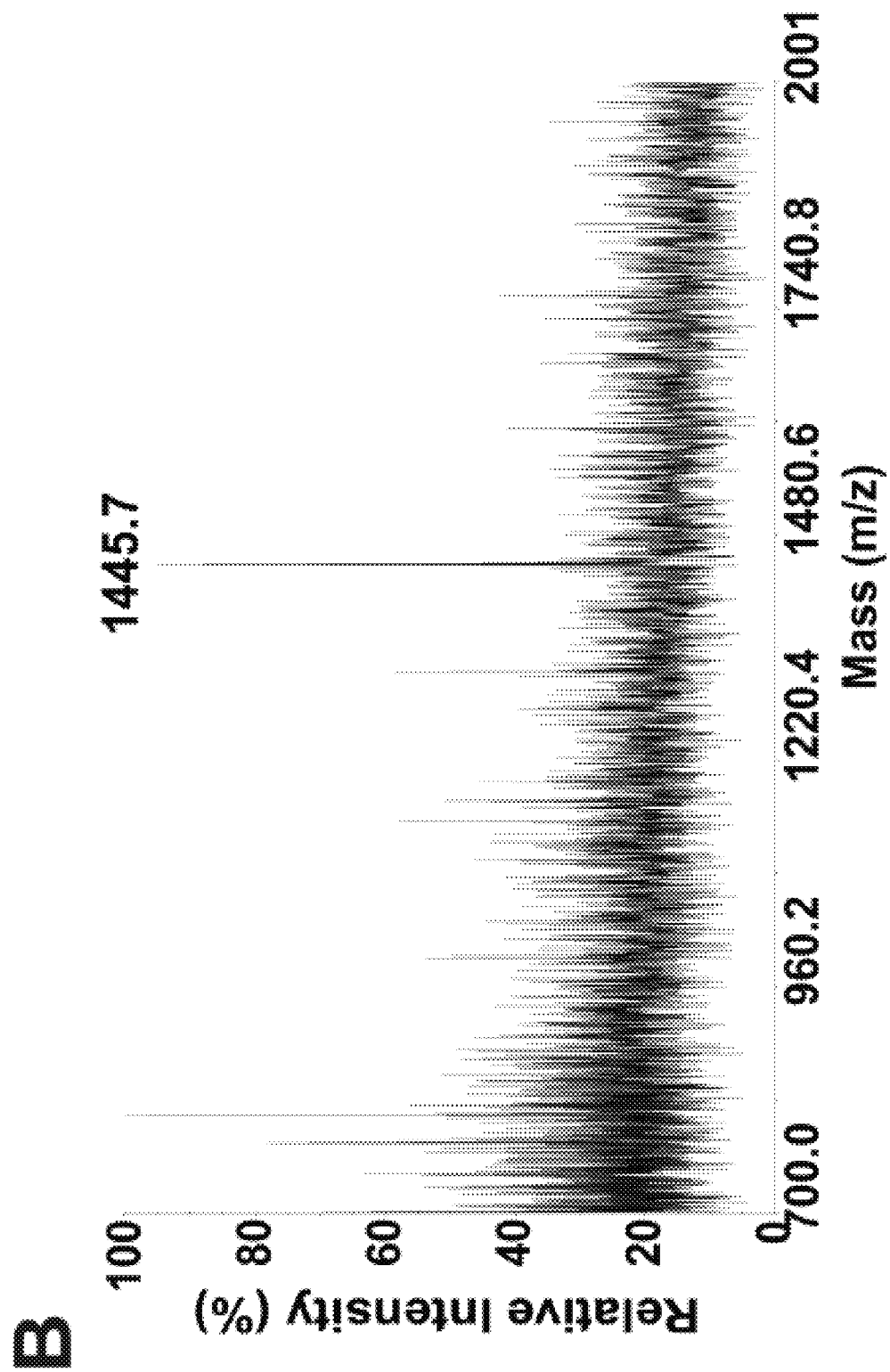
FIG. 11B shows the MALDI-TOF MS spectrum of enriched $fOS_{Cj}$. The enrichment was performed with periplasmic extracts from C. jejuni by solid-phase extraction.
Figure 11C:
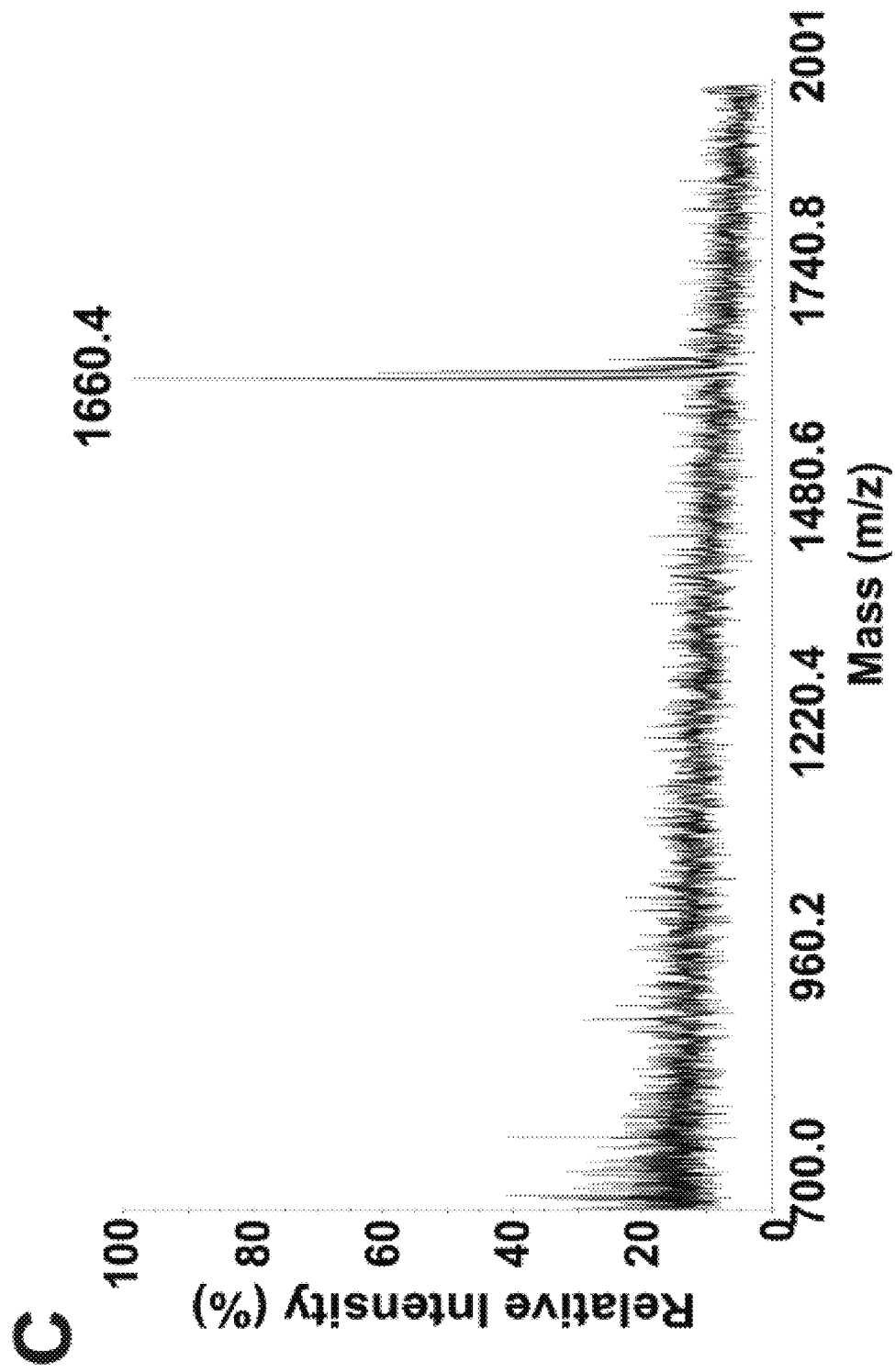
FIG. 11C shows the MALDI-TOF MS spectrum of enriched fOS$_{Cj}$. The enrichment was performed with periplasmic extracts from *C. jejuni* by the hydrazide-functionalized resins.
Figure 11D:
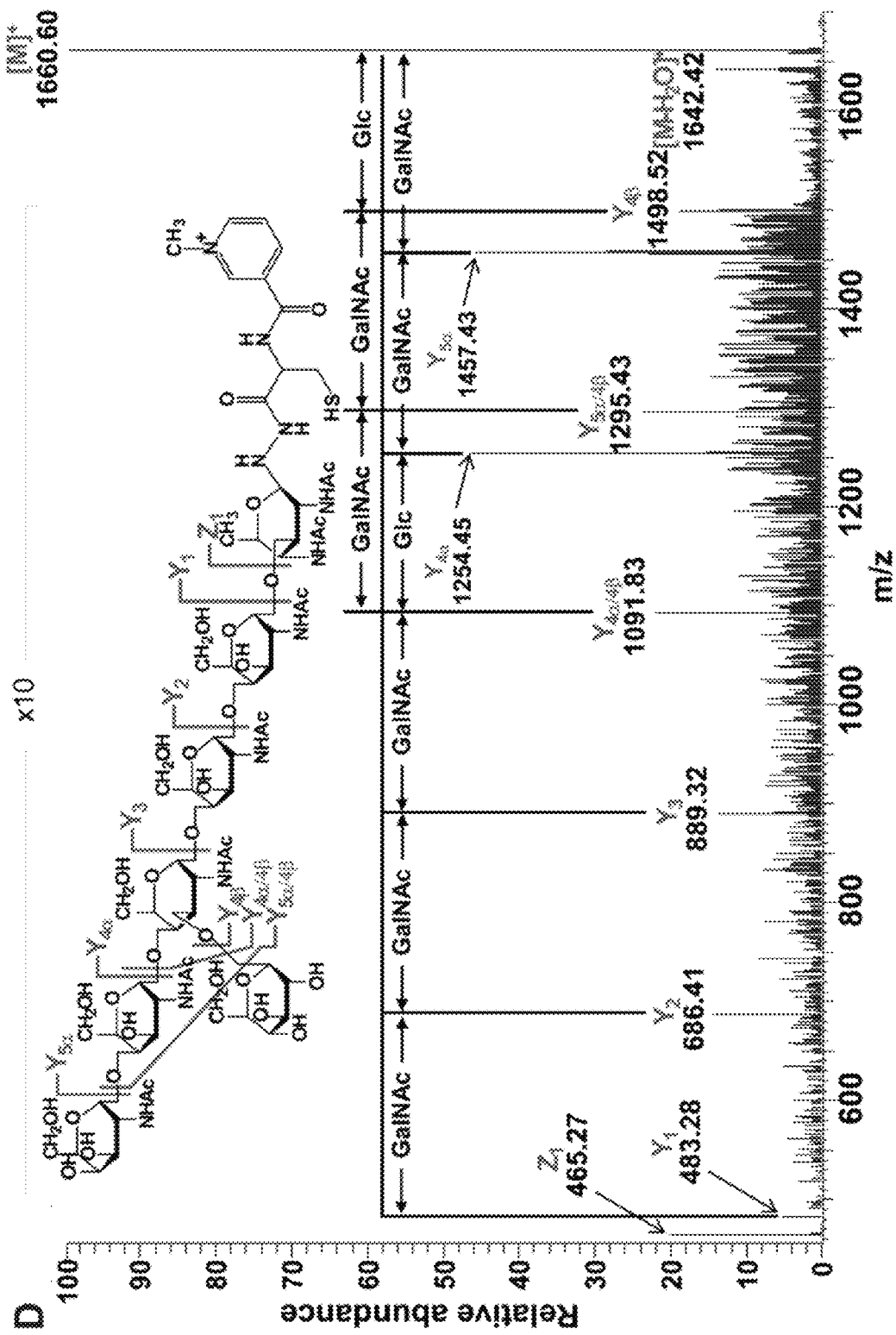
FIG. 11D shows the CID MS/MS spectrum of the fOS$_{Cj}$ from *C. jejuni*. These fragment ions were defined according to the nomenclature introduced by Domon and Costello (Domon et al., (1988) Glycoconj. J. 5:397-409). The glycosidic cleavage was designated as Y and Z (for the reducing end) and B and C (for the non-reducing end), and the cross-ring cleavage was designated as X (for reducing end) and A (for non-reducing end).
Figure 12A:
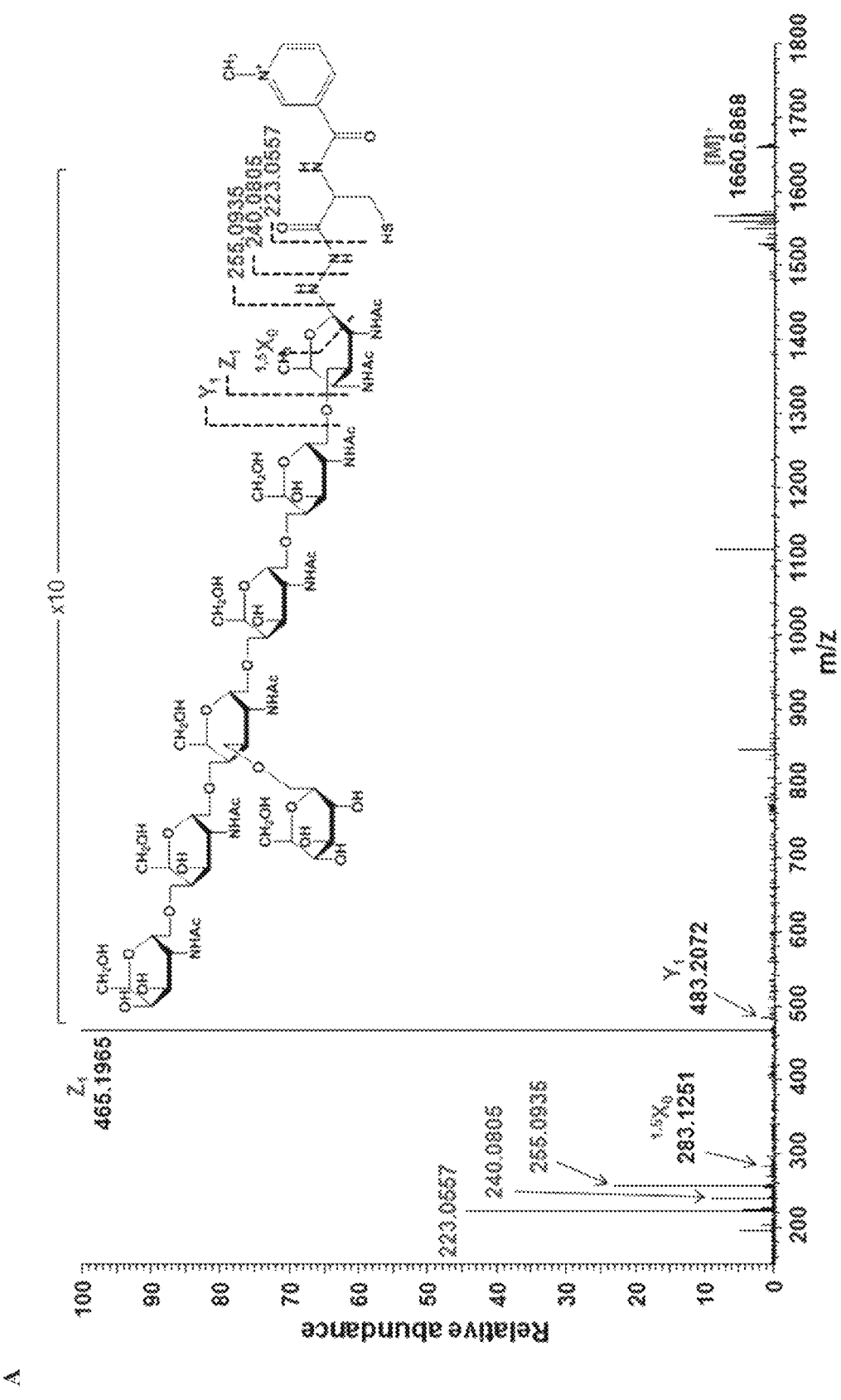
FIG. 12A shows the IRMPD MS/MS spectrum of enriched fOS$_{Cj}$.
Figure 12B:
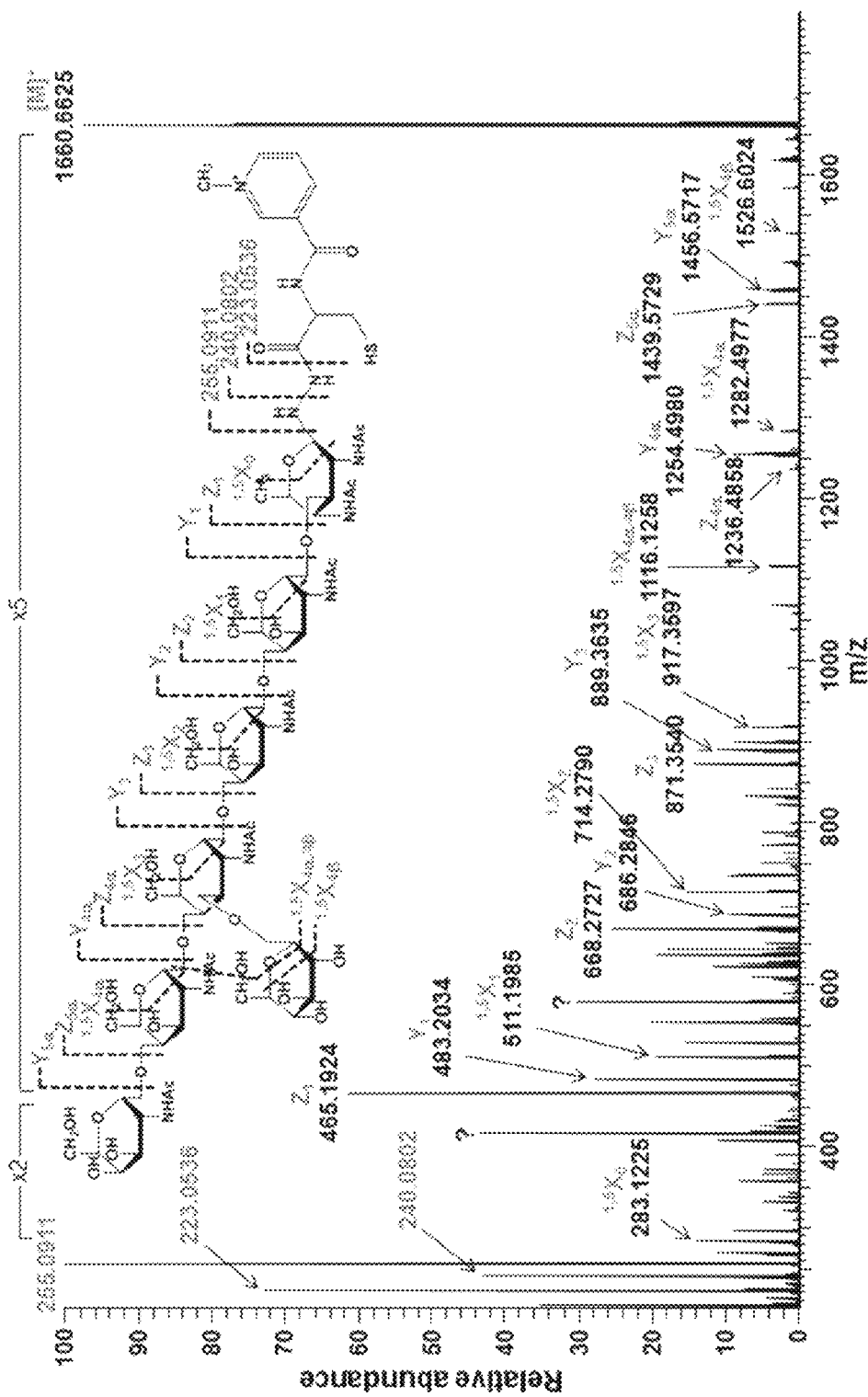
FIG. 12B shows the EID MS/MS spectrum of enriched fOS$_{Cj}$.

The functionality and selectivity of Cyhn resins were examined using fluorescein-labeled glycoproteins. A maltose-binding protein (MBP) possessing bacterial heptasaccharides, which was developed in our previous study, was first oxidized to convert cis-diol to dialdehyde of the glycan structures, followed by the conjugation with fluorescein. The fluorescein-labeled oxidized MBP was incubated with the Cyhn resins. To minimize non-specific protein adsorption, the resins were thoroughly washed with washing buffer containing 8 M urea. The MBP-conjugated resins were examined using Nikon Eclipse 90i Fluorescent microscope (Nikon Instruments Inc., Melville, N.Y.). Fluorescence microscopy analysis showed that the Cyhn resins selectively captured the glycosylated MBP (FIG. 4). Furthermore, the addition of DTT successfully reduced the fluorescence signal of the resin, indicating that the Cyhn molecules were linked to the resin via disulfide bond.

Identification of Bacterial Glycoproteins from a Periplasmic Extract of C. jejuni.

A periplasmic sample was prepared from C. jejuni cells by osmotic lysis. The periplasmic proteins were treated with dithiothreitol, followed by alkylation with iodoacetamide to prevent unwanted conjugation by disulfide formation. Then, the resultant was oxidized prior to the enrichment. Glycoproteins from a periplasmic extract of C. jejuni were selectively captured using the Cyhn-enrichment and then identified by MS. The result from the Cyhn-enrichment was compared with the recently reported result from hydrophilic interaction-enrichment (Scott et al (2011) Mol Cell Proteomics 10, M000031MCP000201). The periplasmic extract of C. jejuni was oxidized and subjected to the enrichment. After washing, the resin-bound proteins were digested by trypsin, then analyzed by high-resolution LTQ-Orbitrap mass spectrometer. As a control experiment, the oxidized periplasmic extract was incubated with bare resins to elucidate non-specific bound proteins. After database searching with the tandem mass spectra, 120 proteins were identified from C. jejuni protein DB with >95% of probability (data not shown). The proteins non-specifically bound to the bare resins were subtracted from the proteins bound to the Cyhn-resins. Among those, 35 proteins were figured out to possess bacterial N-glycosylation sequon (D/E-$X_1$-N-$X_2$-S/T). Tandem MS analysis of the enriched glycopeptides should be performed to figure out.

We established a novel enrichment tool to investigate the bacterial glycome and glycoproteome. This versatile enrichment technique enabled us to efficiently isolate bacterial periplasmic free oligosaccharides as well as glycoproteins, and subsequent MS analyses allowed the identification of those molecules. The following experiment using human cancer cells would show its broader utility in the field of glycoproteomics.

It was reported that free reducing sugars exist in bacterial periplasm perhaps due to the hydrolysis activity of oligosaccharyltransferases, so the structure of the free sugars is expected to reflect the structure of the protein N-linked saccharide (Liu et al. (2006) *Anal Chem* 78, 6081-6087; Nothaft et al (2009) *Proc Natl Acad Sci USA* 106, 15019-15024). Conversely, we may elucidate the existence of NLG system from certain bacteria of interest, whose NLG pathway have yet to be investigated, and identify their N-glycan structures based on the information of their periplasmic free oligosaccharides. We applied the Cyhn-resins to identify free oligosaccharides of *C. jejuni*. As the free heptasaccharide was selectively detected from the periplasmic extract of *C. jejuni*, we will use it to investigate free oligosaccharides from a diverse set of bacterial species to provide information on their NLGs. In addition, bacterial glycoproteins were identified by the enrichment using the Cyhn-conjugated magnetic beads, which allow less non-specific protein binding in comparison of the Sepharose-based resins.

The Cyhn-based enrichment technique, developed in this study, showed high efficient capture in both case of bacterial glycoproteins and free glycans. As the pyridine moiety on the Cyhn molecule can be used as a UV-chromophore due to its optical activity, we will use the Cyhn-conjugation for quantitative glycomics in combination with conventional HPLC. This will allow us to explore the diversity of NLG pathways in a variety of bacterial samples.

Preparation of Bacterial Periplasmic Fraction.

*C. jejuni* NCTC11168 (ATCC 700819) was grown in 500 mL of brain heart infusion (BHI) media at 37° C. under microaerobic condition (1% $O_2$, 10% $CO_2$, 10% $H_2$ and balanced with $N_2$). The cells were pelleted with centrifugation at 3,500 rpm for 10 min. To prepare periplasmic extracts, the cells were lysed by osmotic shock. Briefly, cells were suspended with 30 mL of fractionation buffer (30 mM Tris-HCl containing 20% sucrose and 1 mM EDTA, pH 8.0) at RT for 10 min, on rocking platform. The cells were centrifuged again at 10,000 rpm for 10 min. The pellet was resuspended in 5 mL of ice-cold 5 mM $MgSO_4$ solution and placed on ice for 10 min. After the centrifugation at 13,000 rpm for 10 min, the supernatant was collected as the periplasmic fraction.

Oxidation of Glycoproteins.

One milligram of protein sample was dissolved in 500 µL of oxidation buffer (0.1 M sodium acetate, 150 mM NaCl, pH 5.5), and then 100 µL of 60 mM sodium periodate was added to the solution, resulting in a final concentration of 10 mM. The solution was placed in the dark at RT for 1 h with gentle shaking. After incubation, the samples were placed on Amicon ultra centrifugal filter units (30K molecular weight cutoff, Millipore, Billerica, Mass.) and excess sodium periodate was removed by centrifugation at 12,000 rpm for 10 min by adding 50 mM boric acid (pH 8.5) for conjugation of fluorescein or 50 mM sodium acetate (pH 5.5) for direct capturing.

Conjugation of Oxidized Glycoprotein with Fluorescein.

To conjugate the oxidized glycoproteins with fluorescein, 3 µL of NHS-fluorescein (10 mg/mL in DMSO) was added in 100 µL of the oxidized sample (ca. 100 µg) and it was incubated with at RT for 1 h. After the conjugation, non-reacted NHS-fluorescein was also removed by centrifugation using the centrifugal filter unit, reconstituted with 50 mM sodium acetate (pH 7.0), and then the fluorescein-labeled protein was stored at 4° C. until ready to use.

Enrichment of Free Glycans and Post-Methylation of the Cyhn-Conjugate.

To capture free oligosaccharides, reducing glycans (each 50 nmole) were incubated with 10 µL of Cyhn-6B resins (ca. 10 nmole) at 100° C. for 20 min in 2% (v/v) acetic acid in acetonitrile. After the capturing, the resins were subsequently incubated with 10% of methyl iodide in acetonitrile at RT for 10 h with gentle shaking. The resins were then washed with acetonitrile, followed by deionized water, then released by 50 µL of 10 mM dithiothreitol in 50% methanol for further MALDI-TOF MS analysis.

Glycoprotein-Capturing Using Cyhn-Magnetic Beads.

One hundred milliliter of Cyhn-BcMag beads (ca. 1 µmole) were transferred into a microcentrifuge tube, washed with coupling buffer same as the oxidation buffer, and then the oxidized glycoproteins were added to the Cyhn-6B resins. It was incubated at 37° C. for 24 h without shaking. After the incubation, the resins were washed with washing buffer (8 M urea, 0.4 M ammonium bicarbonate, pH 8.1) for 5 times to alleviate non-specific protein adsorptions. The oxidized glycoproteins were also incubated with bare-resins. After washing, the bound proteins were eluted with 10 mM dithiothreitol, dialyzed with deionized water, dried, and reconstituted with 20 mM ammonium bicarbonate buffer (pH 7.0) for further typsin digestion.

nanoLC-MS Experiments and Database Analysis.

The eluted glycoproteins were tryptic digested for nanoLC-MS analysis using the filter aided sample preparation (FASP) method developed by Mann group (Wisniewski et al. (2009) *Nature Methods* 6, 359-362). After digestion, the supernatant was desalted using a Macrotrap Peptide cartridge, dried, and resuspended in 2% acetonitrile with 0.1% formic acid for nanoflow nanoLC-ESI-MS/MS analysis.

Bacterial Strains and Materials

*Campylobacter jejuni* NCTC11168 (#700819), *C. concisus* RM5485 (#BAA-1457), *Desulfovibrio desulfuricans* G20 (#BAA-1058) and *D. vulgaris* Hildenborough (#29579) were from ATCC (Manassas, Va.). Iodomethane and p-nitrophenyl phosphate substrate were obtained from Sigma-Aldrich (St. Louis, Mo.). Alkaline phosphatase-conjugated lectins were purchased from EY Laboratories Inc. (San Mateo, Calif.). All other chemicals were of analytical grade.

Cell Culture

*C. jejuni* was grown with brain heart infusion (BHI; Difco Laboratories Inc, Detroit, Mich.) medium and *C. concisus* were cultured with *Brucella* Broth (Difco) with 2% yeast extract under microaerobic condition (1% $O_2$, 10% $CO_2$, 10% $H_2$ and balanced with $N_2$) at 37° C. overnight. *D. desulfuricans* and *D. vulgaris* were cultivated with modified Baar medium (ATCC medium 1249) in anaerobic chamber (10% $CO_2$, 10% $H_2$ and 80% $N_2$) at 30° C. overnight. Each cell culture was inoculated to 400 mL culture media and incubated for 24 h.

Bacterial Periplasmic Fractionation

Cells were harvested from cell cultures using centrifugation at 3,500 rpm for 10 min. Periplasmic extraction was performed using an osmotic shock method. Briefly, cell pellets were resuspended with 30 mM Tris-HCl (pH 8.0) containing 20% sucrose and 1 mM $Na_2$EDTA then incubated at room temperature (RT) for 10 min on a rocking platform. After centrifugation at 10,000 rpm for 10 min, the pellets were resuspended with cold 5 mM $MgSO_4$ solution then incubated on ice for 10 min. Periplasmic supernatants were collected using centrifugation at 13,000 rpm for 10 min, then applied on an Amicon ultra centrifugal filter units (10K molecular weight cutoff, Millipore, Billerica, Mass.) to remove periplasmic proteins. The flow-through was stored at 4° C. prior to use.

Solid-Phase Extraction of Free Oligosaccharides fOS were extracted from periplasmic samples using a Carbograph Extract-Clean™ cartridge (150 mg, 4 mL, Grace, Deerfield, Ill.). The solvent system was as follows: 0.1% (w/v) trifluoroacetic acid (TFA) in 50% acetonitrile/50% water (solvent A) and 0.1% (w/v) TFA in 5% acetonitrile/95% water (solvent B). The cartridge was washed with 30% acetic acid in water, washed with HPLC-grade water, and then primed with 3 mL of solvent A followed by 6 mL of solvent B. The periplasmic sample was applied to the column and then washed with water and solvent B. The fOS were eluted with 2×0.5 mL of solvent A and then dried under vacuum. The extracted fOS were reconstituted in 100 μL of deionized water for MALDI-TOF MS analysis.

Enrichment of Free Oligosaccharides

Ten microliter of the fOS extracts were incubated with 10 μL of hydrazide-functionalized resin (ca. 10 nmol), which were previously developed in our group (K. S. Jang et al., submitted for publication), at 100° C. for 20 min in 200 μL of 2% (v/v) acetic acid in acetonitrile. After conjugation, the resin was subsequently incubated with 10% of methyl iodide in acetonitrile at RT for 10 h with gentle shaking. The resin was washed with acetonitrile, followed by deionized water. The enriched fOS were released by 100 μL of 10 mM dithiothreitol in 50% methanol for further MS analysis.

MALDI-MS Analysis

The extracted fOS solution (0.5 μL) was applied to a MALDI target followed by 2,5-dihydroxybenzoic acid (DHB, Sigma-Aldrich) matrix solution (i.e.; 30 mg/mL in 70% acetonitrile/30% water [v/v], 0.5 μL). The fOS were analyzed on a Voyager DE PRO MALDI-TOF mass spectrometer (PerSeptive Biosystems, Framingham, Mass.) operating in reflector and positive ion modes. For all experiments, the accelerating voltage was held at +20 kV, grid voltage at 75%, and guide wire at 0.004%; delay was 100 ns. Mass spectra were acquired from 300 laser shots.

LTQ FT-ICR Analysis

To obtain structural information of enriched fOS, MS/MS analysis was performed on a 7T LTQ FT-ICR Ultra mass spectrometer (Thermo Fisher Scientific., Bremen, Germany) with positive ion mode at spray voltage of 2.2 kV. Samples dissolved in 50% methanol including 2% acetic acid were directly infused into the mass spectrometer at a flow rate of 1 μL/min using a syringe pump. The heated capillary was maintained at a temperature of 200° C. Precursor ions were isolated in the linear ion trap, with an isolation window of 5-10 Da. CID was performed in the linear ion trap with helium as the collision gas. IRMPD and EID were performed in the ICR analyzer. For CID the automatic gain control (AGC) target value was set at $5 \times 10^4$ ions and for IRMPD and EID experiments at $1 \times 10^5$ ions. The maximum ion injection times were 1500 ms for CID, and 2000-2500 ms for IRMPD and EID. In order to achieve optimal fragmentation the collision energy, the irradiation times, the laser power and the cathode voltages were adjusted for each precursor ion. CID was carried out with a normalized collision energy of 15%-20% and 30 ms activation time. MUD experiments were performed with a continuous 20 W, 10.6 μm, $CO_2$ laser (Synrad, Mukilteo, Wash.) at 15-20% laser power and photon irradiation times of 50 ms. EID experiments were carried out with an indirectly heated dispenser cathode (Heatwave, Watsonville, Calif.) at a cathode potential of −20 to −60 V and irradiation time of 50-100 ms.

All publications and patents cited herein are hereby incorporated by reference in their entirety.

Those skilled in the art will recognize, or be able to ascertain using no more than routine experimentation, many equivalents to the specific embodiments of the invention described herein. Such equivalents are intended to be encompassed by the following claims.

The invention claimed is:

1. A compound having a structure of Formula (II):

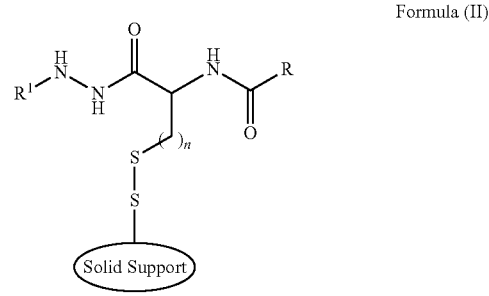

Formula (II)

or a salt thereof, wherein:

n is an integer from 1-10;

R is a nitrogen-containing ring capable of forming a salt; wherein the nitrogen-containing ring is a ring selected from the group consisting of pyridyl, pyridazinyl, pyrazinyl, quinoxalyl, indolizinyl, quinazolinyl, purinyl, quinolinyl, pyrimidinyl, pyrrolyl, pyrazolyl, tetrazolyl, imidazolyl, triazolyl, indolyl, piperidinyl, piperazinyl, and pyrrolidinyl; and $R^1$ is H or saccharide.

2. The compound according to claim 1, wherein R is pyridyl.

3. The compound according to claim 1, wherein n=1.

UNITED STATES PATENT AND TRADEMARK OFFICE
CERTIFICATE OF CORRECTION

PATENT NO. : 9,541,558 B2
APPLICATION NO. : 14/017744
DATED : January 10, 2017
INVENTOR(S) : William M. Clemons et al.

Page 1 of 1

It is certified that error appears in the above-identified patent and that said Letters Patent is hereby corrected as shown below:

In the Specification

In Column 1, at Lines 17-21, please replace:
"This invention was supported in part by the United States Government under National Science Foundation Career grant 1057143 and National Institutes of Health Pioneer Award 5DP1GM105385. The Government may have certain rights in this invention."
With:
--This invention was made with government support under Grant No. GM105385 awarded by the National Institutes of Health and under Grant No. 1057143 awarded by the National Science Foundation. The government has certain rights in the invention.--

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*